United States Patent [19]

Stiles et al.

[11] Patent Number: 6,075,184
[45] Date of Patent: Jun. 13, 2000

[54] PURIFIED PROTEINS, RECOMBINANT DNA SEQUENCES AND PROCESSES FOR PRODUCING CAFFEINE FREE BEVERAGES

[75] Inventors: John I. Stiles, Kaneahe; Istefo Moisyadi; Kabi Raj Neupane, both of Honolulu, all of Hi.

[73] Assignee: University of Hawaii, Honolulu, Hi.

[21] Appl. No.: 08/622,679

[22] Filed: Mar. 26, 1996

[51] Int. Cl.$^7$ ............................ C12N 15/29; C12N 15/82; A01H 4/00; A01H 5/00
[52] U.S. Cl. ........................ 800/298; 800/295; 800/278; 536/23.6; 536/24.1; 435/468; 435/419; 435/320.1
[58] Field of Search .................... 536/23.6, 24.1; 435/468, 419, 320.1; 800/278, 295, 298

[56] References Cited

FOREIGN PATENT DOCUMENTS

| WO 91/01375 | 2/1991 | WIPO . |
| WO 92/04456 | 3/1992 | WIPO . |
| WO 96/07742 | 3/1996 | WIPO . |
| WO 96/19103 | 6/1996 | WIPO . |
| WO 96/21027 | 7/1996 | WIPO . |

OTHER PUBLICATIONS

"Are Xanthosine and 7–Methylxanthosine Caffeine Precursors?" by Schulthess & Baumann (Received in revised form Feb. 7, 1995).

"A Visible Marker for Antisense mRNA expression in plants: Inhibition of chlorophyll synthesis with a glutamate–1–semialdehyde aminotransferase antisense gene" by Höfgen, et al. (Proc. Natl. Acad. Sci. USA, vol. 91, pp. 1726–1730, Mar. 1994, Plant Biology).

"Purine and Purine Alkalois Metabolism in Camellia and Coffea Plants" by Suzuki, et al. (Phytochemistry Review Article No. 68. 1992, vol. 31, No. 8, pp. 2575–2584).

*Primary Examiner*—Lynette R. F. Smith
*Assistant Examiner*—Thana Haas
*Attorney, Agent, or Firm*—Jones, Day, Reavis & Pogue

[57] ABSTRACT

Purified proteins, DNA sequences that code on expression therefore and recombinant DNA molecules, including hosts transformed therewith, for transforming coffee plants to suppress the expression of caffeine. The DNA sequences and recombinant DNA molecules are characterized in that they code on expression for an enzyme in the pathway for caffeine synthesis in coffee. Coffee plants transformed with DNA molecules that code on transcription for mRNA that is antisense to mRNA that codes on expression for at least one enzyme in the pathway for caffeine biosynthesis.

42 Claims, 8 Drawing Sheets

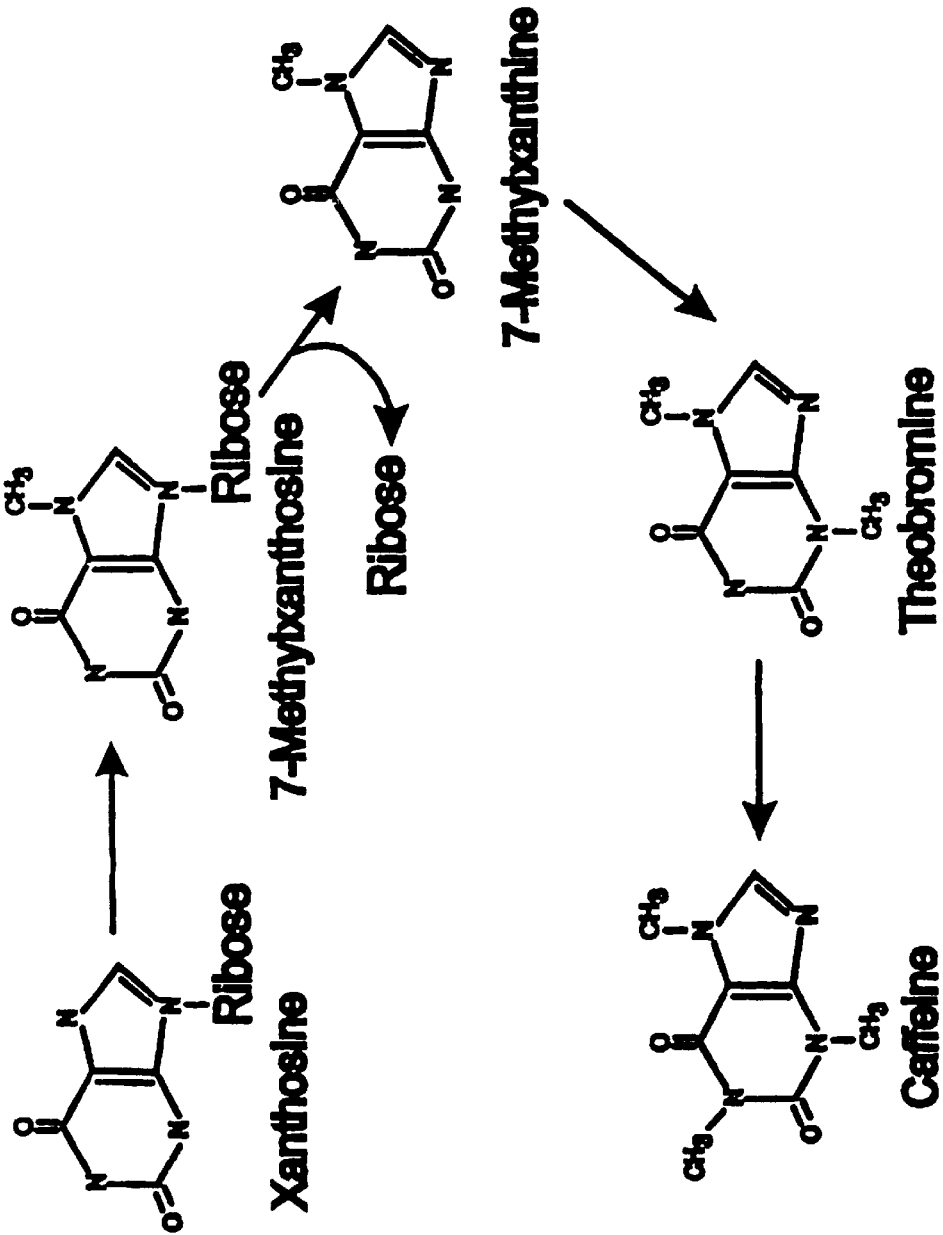
Figure 1. Caffeine Biosynthetic Pathway

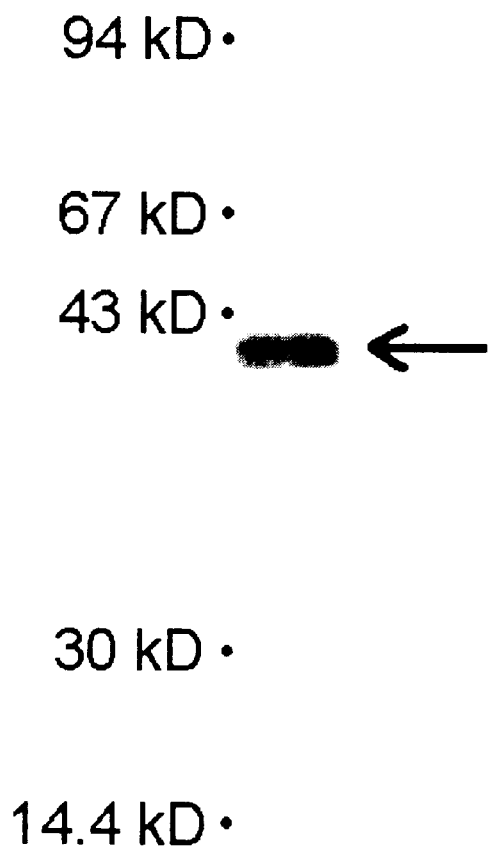
Figure 2. Polyacrylamide gel of purified xanthosine-$N^7$-methyl transferase
94 kD •
67 kD •
43 kD •
30 kD •
14.4 kD •

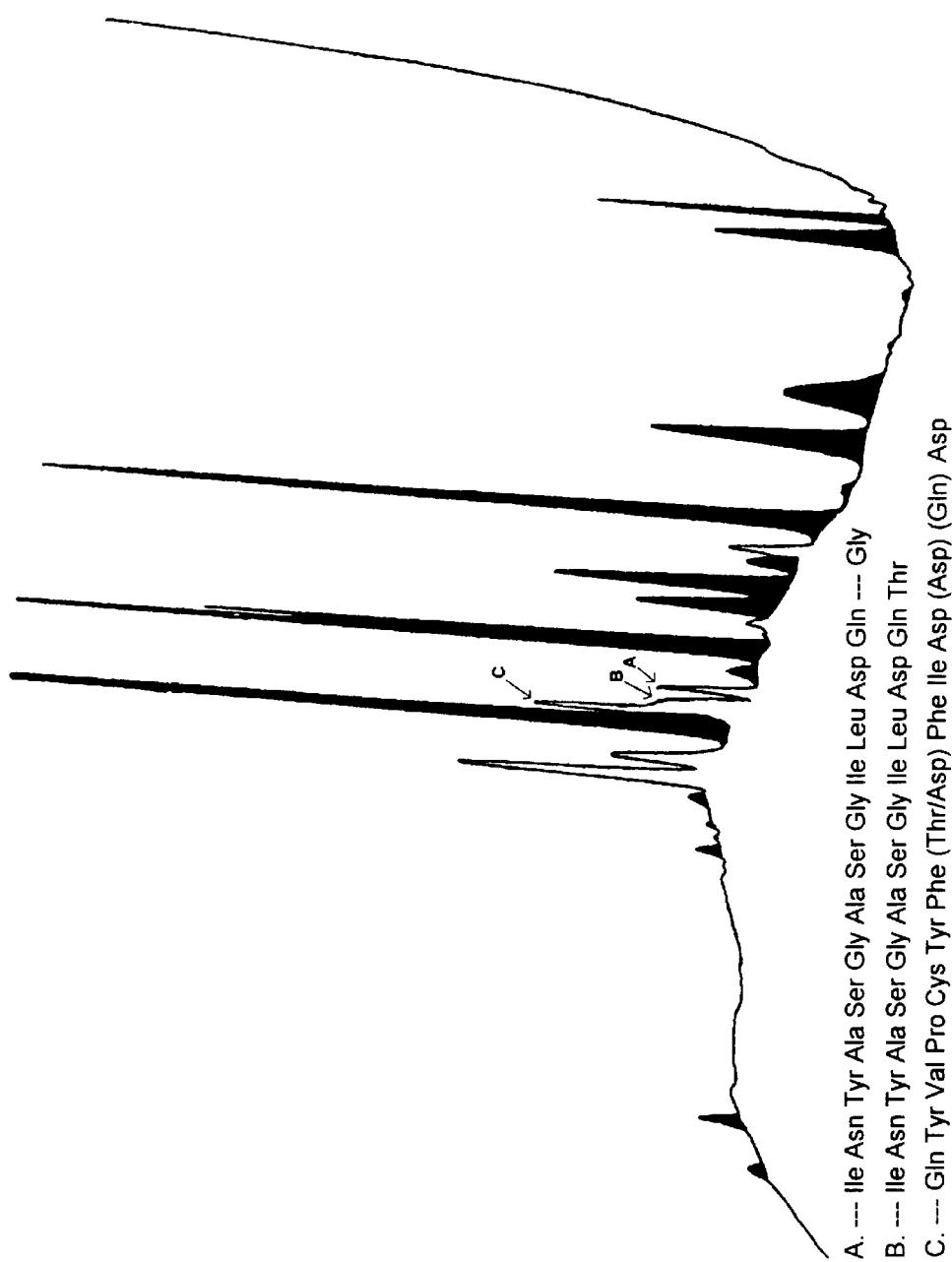
Figure 3. HPLC separation of tryptic digest of xanthosine-N⁷-methyl transferase
A. — Ile Asn Tyr Ala Ser Gly Ala Ser Gly Ile Leu Asp Gln — Gly
B. — Ile Asn Tyr Ala Ser Gly Ala Ser Gly Ile Leu Asp Gln Thr
C. — Gln Tyr Val Pro Cys Tyr Phe (Thr/Asp) Phe Ile Asp (Asp) (Gln) Asp Figure 4. Oligonucleotides synthesized from peptides Fragment A.  --- Ile Asn Tyr Ala Ser Gly Ala Ser Gly Ile Leu Asp Gln --- Gly
Fragment B.  --- Ile Asn Tyr Ala Ser Gly Ala Ser Gly Ile Leu Asp Gln Thr
Primer 1     5'ATI AA$_T^C$ TA$_T^C$GCI TCI GGI GC
Primer 2     5'ATI AA$_T^C$ TA$_T^C$GCI AG$_T^C$ GGI GC
Primer 3     3'TAI TT$_A^G$ AT$_A^G$CGI AGI CCI GC
Primer 4     3'TAI TT$_A^G$ AT$_A^G$CGI TC$_A^G$ CCI GC Fragment C. --- Gln Tyr Val Pro Cys Tyr Phe $_{Asp}^{Thr}$ Phe Ile Asp (Asp) (Gln) Asp Primer 5     5'CA$_A^G$ TAT GTI CCI TGT TAT TT Primer 6     3'GTT AT$_A^G$CAI GGI AC$_A^G$ AT$_A^G$AA

FIGURE 5

```
CCTCTGACTT GCTAAACCTA CCATTACCTT TTTCTTCTTG TCATCTGCAT      50
TCATGGCTTT TGTAGCCAGG CAATGGTTTC TCCTATCCAT CATTAATGTA     100
GTGGTTGTCT GTTTCTTGAA ACCATTTGCC CTAGGCGAAC AACAGGTCCC     150
TTGCTACTTC ATTTTGGAG  ACTCACAAGA TGACAATGGC AACAATAATC     200
ACCTGAACAC CACTGCCAGG GCAAATTATC CACCTTACGG CATTGATTTC     250
CCAGAAGGTC CAACTGGTCG CTTCACCAAT GGTCGAAATC ATGCAGACTT     300
CATTGGTGAG CTCCTTGGAT TTGACAGCTA CATACCTCCA TTTGCAAATA     350
CAAAAGGCCG GGATATCACT AAAGGCATTA ATTATGCTTC GGGAGCATCT     400
GGAATTCTTG ATCAGACCGG TCGTCACCTG GGCGATCTCT TCAGCTTCAA     450
CGAACAATTG CACAATCACG AGAGAGCAAT TTCGCGCATC GTGCGGTTGA     500
TTGGAAACAG ATCTGCAACA AAAGAATATC TAGCCAAATG TCTGTACACT     550
GTTGCATTGG GGAATAATGA TTACATCAAC AACTACTTGT TGCCAGAATA     600
TTATCCTACC AGCCACCTAT ATACTCCAAG AGAATTTGCC AGCTTGTTAA     650
TTAGGCATTA TTCTCAGCAA CTACGGACTT TGTACAGATT GGGGGCAAGA     700
AAAATAGCCG TTTTTGGGCT TGGTTGGCTT GGCTGCATAC CTGCTGAGTT     750
ATCTACAGAT GGTAACTGTG TGGATTCTAT TAACGAGGAA GTTCTGTTAT     800
TCAATGACAA GCTCAAGCCA CTGGTTGATG AACTGAATAC CGAGTTAAGC     850
GGTGCACAAT TTCTTTATGT AGATGTGATA GCAATCAATT TGAACAATTT     900
ATCCACCCCT GCAGAAATTA CAATTGGCAA TGCACCATGC TGCAACGTGT     950
CTGCAGCAGT TGCTGGTGGA CAGTGTATTC CTGGGCAAAT TCCCTGCAGC    1000
AACAGGAACC AATATTATTT TTGGGATGAT TTCCATCCCA GTGAAGTAGT    1050
CAATGAAGCA TATTCAAGAT TAGCATATTC TGCGTTATCC TCATTACTTG    1100
ATGCTGATCC TCTTGCCATT GGCGGCCTAA CAGGCAAAAA CTGTCATGAT    1150
```

FIGURE 5 (continued)

```
AAAGTGAAGA TACAATAGAC TGTATCTATG TGTCCCATGA TATTTCTATA    1200

TTCCAAGTTT CCGACAAGTC AAACTCAATG TAATAAAACT TGAGAGTCCG    1250

AATGTGCTAG TGTGATGTTA TCTCCTCAAT GGAAACAATA TGTTATCATT    1300

AATCTCAGAC TATTTATAAT TACTATTAAA AAAAAAAAAA AAAAAA        1347
```

FIGURE 6

```
Met Ala Phe Val Ala Arg Gln Trp Phe Leu Leu Ser Ile Ile Asn
 1               5                  10                   15

Val Val Val Val Cys Phe Leu Lys Pro Phe Ala Leu Gly Glu Gln
                20                  25                   30

Gln Val Pro Cys Tyr Phe Ile Phe Gly Asp Ser Gln Asp Asp Asn
                35                  40                   45

Gly Asn Asn Asn His Leu Asn Thr Thr Ala Arg Ala Asn Tyr Pro
                50                  55                   60

Pro Tyr Gly Ile Asp Phe Pro Glu Gly Pro Thr Gly Arg Phe Thr
                65                  70                   75

Asn Gly Arg Asn His Ala Asp Phe Ile Gly Glu Leu Leu Gly Phe
                80                  85                   90

Asp Ser Tyr Ile Pro Pro Phe Ala Asn Thr Lys Gly Arg Asp Ile
                95                  100                  105

Thr Lys Gly Ile Asn Tyr Ala Ser Gly Ala Ser Gly Ile Leu Asp
                110                 115                  120

Gln Thr Gly Arg His Leu Gly Asp Leu Phe Ser Phe Asn Glu Gln
                125                 130                  135

Leu His Asn His Glu Arg Ala Ile Ser Arg Ile Val Arg Leu Ile
                140                 145                  150

Gly Asn Arg Ser Ala Thr Lys Glu Tyr Leu Ala Lys Cys Leu Tyr
                155                 160                  165

Thr Val Ala Leu Gly Asn Asn Asp Tyr Ile Asn Asn Tyr Leu Leu
                170                 175                  180

Pro Glu Tyr Tyr Pro Thr Ser His Leu Tyr Thr Pro Arg Glu Phe
                185                 190                  195

Ala Ser Leu Leu Ile Arg His Tyr Ser Gln Gln Leu Arg Thr Leu
                200                 205                  210

Tyr Arg Leu Gly Ala Arg Lys Ile Ala Val Phe Gly Leu Gly Trp
                215                 220                  225
```

FIGURE 6 (continued)

```
Leu Gly Cys Ile Pro Ala Glu Leu Ser Thr Asp Gly Asn Cys Val
                230                 235                 240

Asp Ser Ile Asn Glu Glu Val Leu Leu Phe Asn Asp Lys Leu Lys
                245                 250                 255

Pro Leu Val Asp Glu Leu Asn Thr Glu Leu Ser Gly Ala Gln Phe
                260                 265                 270

Leu Tyr Val Asp Val Ile Ala Ile Asn Leu Asn Asn Leu Ser Thr
                275                 280                 285

Pro Ala Glu Ile Thr Ile Gly Asn Ala Pro Cys Cys Asn Val Ser
                290                 295                 300

Ala Ala Val Ala Gly Gly Gln Cys Ile Pro Gly Gln Ile Pro Cys
                305                 310                 315

Ser Asn Arg Asn Gln Tyr Tyr Phe Trp Asp Asp Phe His Pro Ser
                320                 325                 330

Glu Val Val Asn Glu Ala Tyr Ser Arg Leu Ala Tyr Ser Ala Leu
                335                 340                 345

Ser Ser Leu Leu Asp Ala Asp Pro Leu Ala Ile Gly Gly Leu Thr
                350                 355                 360

Gly Lys Asn Cys His Asp Lys Val Lys Ile Gln
                365                 370
```

PURIFIED PROTEINS, RECOMBINANT DNA SEQUENCES AND PROCESSES FOR PRODUCING CAFFEINE FREE BEVERAGES

This application relates to purified proteins, recombinant DNA sequences, hosts transformed therewith and processes for producing caffeine-free beverages and food products. More particularly, this application relates to purified proteins, and recombinant DNA sequences that suppress the expression of caffeine in coffee plants, and in fruit harvested therefrom. The invention produces stable lines of caffeine free coffee plants whose fruit, after roasting and grinding, can be used to prepare caffeine free coffee. It is expected that the invention can be used to suppress caffeine synthesis in tea (*Camilla sinensis*) and cola (*Cola acuminata*), as well as related alkaloids in chocolate (*Theobroma cacao*).

BACKGROUND OF THE INVENTION

Coffee is prepared from the roasted ground beans of the plants of the genus Coffea, generally from the species *C. arabica*. Coffee plants produce the alkaloid caffeine, which is present in their dried fruit, coffee beans. Because many coffee drinkers prefer coffee without caffeine, a number of processes have been developed to remove caffeine from coffee beans. All of these processes result in the removal of substances other than caffeine from the beans, thereby adversely affecting the taste of coffee brewed from the treated beans. Although a few naturally occurring caffeine free coffees and related genera are known (Mascarocoffea spp. and *Coffea bengalensis*), they have no commercial value. (Charrier and Berthaud, "Variation of Caffeine Content In The Coffea Genus", *Cafe' Cacao The'*, 14:251–264 (1975)). Accordingly, there is a need for a method for producing decaffeinated coffee beans that does not result in the removal of substances from the beans other than caffeine.

Caffeine is a naturally occurring purine alkaloid produced by coffee and tea plants, among others. It is believed that caffeine synthesis protects the plants from insects. Coffee plants synthesize caffeine from the nucleoside xanthosine in four sequential reactions as shown in FIG. 1. For review see Suzuki, T., Ashihara, H. and Waller, G. R., *Phytochemistry* 31:2575 (1992). The first step in the pathway is the methylation of the nucleoside xanthosine by S-adenosylmethionine, which is catalyzed by the enzyme xanthosine $N^7$ methyl transferase (XMT). The product, 7-methylxanthosine is hydrolyzed (a ribose is removed) to 7 methylxanthine, and undergoes further methylations to theobromine and caffeine. It is to be expected that interruption of this sequence of synthetic reactions would block caffeine synthesis.

Accordingly, a strategy for selectively eliminating caffeine from coffee plants is to prevent synthesis of specific enzymes in the pathway for caffeine biosynthesis. In one embodiment this invention relates to genetic alteration of coffee plants to eliminate synthesis of XMT. In the presently preferred embodiment, synthesis of XMT is suppressed by transforming coffee plants with a DNA sequence that codes on transcription for a messenger RNA (mRNA) that is antisense to the mRNA that codes on expression for XMT. The invention may be generalized to produce other caffeine free beverages and food products, including tea, cocoa, and other chocolate-based beverages or foods.

SUMMARY OF INVENTION

Purified proteins, DNA sequences that code on expression therefore and recombinant DNA molecules, including hosts transformed therewith, for transforming coffee plants to suppress the expression of caffeine. The DNA sequences and recombinant DNA molecules are characterized in that they code on expression for an enzyme, xanthosine $N^7$ methyl transferase (XMT), that is the first step in the pathway for caffeine synthesis in coffee. The base sequence of that DNA and the predicted amino acid sequence of XMT is provided.

Coffee plants are transformed with DNA molecules that code on transcription for mRNA that is antisense to mRNA that codes on expression for at least one enzyme in the pathway for caffeine biosynthesis. The antisense RNA binds to XMT mRNA, thereby inactivating the mRNA encoding the first step in the pathway for caffeine synthesis. The result is that the transformed plants are incapable of synthesizing caffeine, though other aspects of their metabolism is not affected.

BRIEF DESCRIPTION OF THE DRAWINGS

FIG. 1 is a schematic drawing of the pathway for caffeine synthesis in *Coffea arabica*.

FIG. 2 is a photograph of a silver stained SDS PAGE gel of purified xanthosine $N^7$ methyl transferase.

FIG. 3 is a densitometric plot showing elution of tryptic fragments of purified xanthosine $N^7$ methyl transferase following HPLC separation.

FIG. 4 is a description of the oligonucleotide primers used to screen the cDNA library cDNA encoding xanthosine $N^7$ methyl transferase.

FIG. 5 is the base sequence of the cDNA that encodes xanthosine $N^7$ methyl transferase.

FIG. 6 with the predicted amino acid sequence of xanthosine $N^7$ methyl transferase.

DETAILED DESCRIPTION OF THE INVENTION

In order that the invention herein described may be more fully understood, the following detailed description is set forth. In the description the following terms are employed:

Nucleotide—A monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is called a nucleoside. The base characterizes the nucleotide. The four DNA bases are adenine ("A"), guanine ("G"), cytosine ("C"), and thymine ("T"). The four RNA bases are A, G, C, and uracil ("U").

DNA Sequence—A linear array of nucleotides connected one to the other by phosphodiester bonds between the 3' and 5' carbons of adjacent pentoses.

Codon—A DNA sequence of three nucleotides (a triplet) which encodes through mRNA an amino acid, a translation start signal or a translation termination signal. For example, the nucleotide triplets TTA, TTG, CTT, CTC, CTA and CTG encode for the amino acid leucine ("Leu"), TAG, TAA and TGA are translation stop signals and ATG is a translation start signal, which also encodes the amino acid methionine ("MET").

Polypeptide—A linear array of amino acids connected one to the other by peptide bonds between the amino and carboxy groups of adjacent amino acids.

Genome—The entire DNA of a cell or a virus. It includes inter alia the structural gene coding for the polypeptides of the substance, as well as promoter, transcription and translation initiation and termination sites.

Gene—A DNA sequence which encodes through its template or messenger RNA ("mRNA") a sequence of amino acids characteristic of a specific polypeptide.

Transcription—The process of producing mRNA from a gene or DNA sequence.

Translation—The process of producing a polypeptide from mRNA.

Expression—The process undergone by a gene or DNA sequence to produce a polypeptide. It is a combination of transcription and translation.

Plasmid—A nonchromosomal double-stranded DNA sequence comprising an intact "replicon" such that the plasmid is replicated in a host cell. When the plasmid is placed within a unicellular organism, the characteristics of that organism may be changed or transformed as a result of the DNA of the plasmid. For example, a plasmid carrying the gene for tetracycline resistance (TETR) transforms a cell previously sensitive to tetracycline into one which is resistant to it. A cell transformed by a plasmid is called a "transformant."

Phage or Bacteriophage—Bacterial virus many of which consist of DNA sequences encapsidated in a protein envelope or coat ("capsid").

Cloning Vehicle—A plasmid, phage DNA, cosmid or other DNA sequence which is able to replicate in a host cell, characterized by one or a small number of endonuclease recognition sites at which such DNA sequences may be cut in a determinable fashion without attendant loss of an essential biological function of the DNA, e.g., replication, production of coat proteins or loss of promoter or binding sites and which contain a marker suitable for use in the identification of transformed cells, e.g., tetracycline resistance or ampicillin resistance. A cloning vehicle is often called a vector.

Cloning—The process of obtaining a population of organisms or DNA sequences derived from one such organism or sequence by asexual reproduction.

Recombinant DNA Molecule or Hybrid DNA—A molecule consisting of segments of DNA from different genomes which have been joined end-to-end outside of living cells and able to be maintained in living cells.

cDNA—A DNA strand complementary to an mRNA that codes for a particular polypeptide.

Although the strategy for producing caffeine free coffee may be generalized to other enzymes in the pathway for caffeine synthesis in coffee and other caffeine producing plants, in the presently preferred embodiment of this invention, the expression of the first unique enzyme in the pathway, xanthosine $N^7$ methyl transfersase (XMT) is suppressed. While the role of XMT in caffeine synthesis has been elucidated by radiolabeling of precursors, to date the enzyme has not been purified nor has its amino acid sequence been determined. This invention therefore includes substantially purified XMT. The invention further includes the amino acid sequence of tryptic fragments isolated from the purified XMT.

cDNA probes based on portions the amino acid sequence obtained from samples of the purified enzyme were synthesized and a portion of the gene was amplified using PCR. The PCR products were used to screen a cDNA library synthesized from young leaf mRNA to identify transcripts encoding XMT. The positive transcripts were sequenced and approximately 90% of the gene encoding XMT was obtained.

DNA that codes on expression for XMT are incorporated into a pBI-121 transformation vector which includes a kanamycin resistance gene. Successful incorporation of the vectar into plant cells will be monitored by acquisition of antibiotic resistance. The constructs are used to transform coffee somatic embryos in tissue culture. The transformed embryos are thereafter grown into novel coffee plants that do not produce caffeine. Naturally decaffeinated coffee is prepared from roasted ground fruit from these novel plants.

More specifically, fresh leaf tissue from young leaves of *C. arabica* was macerated and protein extracted therefrom. Column purified extracts were assayed for enzymatic activity, by monitoring the methylation of xanthosine using $C^{14}$ labeled S-adenosylmethionine as substrate. The reaction product was confirmed as 7-methylxanthosine by comparing the migration of the labeled reaction product with migration of 3-methylxanthine, 7-methylxanthine, 8-methylxanthine, 7-methylxanthosine, xanthine and xanthosine in each of four different chromatography systems.

The purity of the protein isolates was determined using SDS PAGE electrophoresis and two dimensional gel electrophoresis. Silver staining of one dimensional SDS PAGE gels indicated the presence of a doublet with the enzymatic activity of XMT, with a molecular weight of 36–37 kD as shown in FIG. 2. Each protein was further resolved with isoelectric focusing. The data indicates the presence of isozymes of XMT that may result from post translational modification of the protein; alternatively, there may be a gene family encoding XMT enzymes.

The doublet visualized on SDS PAGE gels was used for protein sequencing. Purified XMT was subjected to partial tryptic digestion to create fragments for further analysis; three peaks were resolved using HPLC. Sequencing was performed by the Protein Structure Laboratory of the University of California, Davis using automated Edman degradation. (Edman, P. and Begg, G., *Eur. J. Biochem.* 1:80). Two unique sequences were resolved, and used to construct primers for probe synthesis. RNA was extracted from coffee leaves. mRNA containing poly ($A^+$) sequences was purified therefrom. A cDNA library was prepared from the poly ($A^+$) mRNA using reverse transcriptase. Double stranded DNA was prepared using DNA polymerase I, and recovered by precipitation. The cDNA was fractionated and inserted into phage for amplification. The cDNA library was screened with a PCR synthesized probe produced using primers based on the DNA sequence expected from the amino acid sequence of the purified XMT. A clone producing a cDNA containing all of the sequences encoding XMT has been identified.

The cDNA corresponding to the gene encoding XMT is used to transform embryonic coffee plants. The plasmid pBI-121 is used as a transforming vector. The sequences corresponding to DNA that codes on expression for XMT is inserted into the plasmid in an inverted orientation adjacent to a cauliflower mosaic virus 35S promoter. RNA transcribed therefrom will be complementary to mRNA that encodes the amino acid sequence of XMT. Complete constructs are amplified in bacterial hosts. The hosts are disrupted and the amplified vector is attached to colloidal gold particles. The gold particles with adherent vectors are inserted into coffee plant protoplasts by propelling the particles at high speed at the cells as described in U.S. Pat. No. 5,107,065. Young plants successfully transformed are identified by antibiotic resistance. The transformed plants do not produce caffeine.

EXAMPLES

A. Purification of Xanthosine-$N^7$-methyltransferase from *C. arabica* L. cv Guatemalan Coffee Leaves Young leaf tissue, less than 5 mm in length (equivalent to the B3 stage (Frischknecht, P. M., Ulmer-Dufek, J. and Baumann, T. W. (1986) *Phytochemistry* 25:613) were collected from trees grown at the University of Hawaii Waimanalo Research Station, Oahu, Hawaii. Leaves were immediately immersed in liquid nitrogen (liquid $N_2$) and stored at −70° C. until used. All subsequent procedures were carried out at 4° C. unless otherwise stated. Leaf tissue (150 g) was macerated in a mortar and pestle under liquid $N_2$ and, while still frozen, transferred to a pre-chilled domestic coffee grinder and ground with a small piece of dry ice for about 30 sec. The powdered tissue was added to a beaker containing 1.5 L of ice cold 80% acetone, 5 mM thiourea, and 12.5 mM β-mercaptoethanol. After mixing on a magnetic stirrer for 45 min, the tissue was recovered by filtration under vacuum in a Buchner funnel containing Whatman No. 1 filter paper. The tissue was washed with 2.5 L of 80% ice cold acetone containing thiourea and β-mercaptoethanol as above, air dried for 20 min and then lyophilized for 48 hours.

The resulting acetone powder was homogenized in a blender with 400 mL of extraction buffer (EB) (0.1 M PIPES [pH 7.0], 0.5 mM $Na_2EDTA$, 0.5 mM $Na_2EGTA$, 5% ascorbic acid, 5 mM dithiothreitol [DTT], 5 mM thiourea, 12 mM L-cysteine HCl, 1% polyethylene glycol (PEG) 20,000, 0.1 mM phenylmethylsulfonyl fluoride [PMSF], and 20 g polyvinylpolypyrrolidone [PVPP]). The slurry was homogenized for 10 min at medium speed, and then transferred into 250 mL centrifuge bottles and centrifuged at 23,000×g for 30 min in a GSA (Dupont-Sorvall) rotor.

The 350 mL crude supernatant obtained was brought to 40% ammonium sulfate (AS) saturation over 30 min by the slow addition of 79.86 g AS powder while being stirred in a beaker surrounded by an ice bath. The mixture was once again transferred to 250 mL centrifuge bottles and centrifuged at 23,000×g for 30 min as above. The 350 mL supernatant obtained was loaded into a 40 mL Macro-Prep (Bio-Rad) methyl hydrophobic interaction chromatography (HIC) column at the flow rate of 2.5 mL/min. All column fractions were monitored for protein using absorbance at 280 nm. The HIC column was washed with pre-equilibration buffer containing 1.7 M AS, 20 mM bis-tris-propane (pH 6.8), and 5 mM DTT until a baseline near zero was established. The column was then stripped with a buffer containing 10 mM tris (pH 7.0), 5 mM DTT, 1 mM $MgCl_2$. The first 15 mL out of the column was discarded and the remaining eluate (200 mL) was loaded under gravity into a 100 mL Affi-Gel blue affinity gel (100–200 mesh, Bio-Rad) column that had the dye Cibacron blue F3GA covalently attached to the matrix. The gel was pre-equilibrated with 10 mM tris (pH 7.0), 5 mM DTT, 1 mM $MgCl_2$ loading buffer. The column was washed extensively with this loading buffer until the baseline stabilized near zero, and the bound proteins were eluted with a buffer containing 10 mM tris (pH 7.0), 5 mM DTT, and 1.5 M sodium chloride (NaCl).

The 142 mL Affi-Gel Blue Gel column eluate was made 1.7 M AS by the slow addition of 31.8 g AS powder while being stirred for 30 min in a beaker surrounded by an ice bath. The slurry was centrifuged in 250 mL centrifuge bottles at 23,000×g for 30 min as above, and the supernatant loaded into an FPLC Phenyl-Sepharose column XK 26/20 (Pharmacia) at 23° C. The column was pre-equilibrated with a buffer containing 20 mM bis-Tris-Propane (pH 6.8), 5 mM DTT, and 1.7 M AS. When a baseline was established near zero the proteins were eluted out of the column in a 40 min reverse gradient of 1.7 M AS to 0 M AS at a flow rate of 5 mL/min, collecting 1 min fractions. The 0 M AS elution buffer contained 10 mM tris (pH 7.0), 5 mM DTT, and 1 mM $MgCl_2$.

Activity assays on the fractions collected indicated that the majority of enzymic activity for xanthosine-$N^7$-methyltransferase was concentrated in fractions 49 to 54. These fractions were pooled into 30 mL final volume, and then loaded into a 6 mL ATP-agarose column (Sigma Chemicals, A2767) by gravity at 4° C. The column was pre-equilibrated with 10 mM tris (pH 7.0), 5 mM DTT, and 1 mM $MgCl_2$. After stabilization of the baseline, the column was stripped with 20 mL of pre-equilibration buffer containing 100 μM xanthosine, and washed with an additional 40 mL pre-equilibration buffer. Both column eluates were pooled and loaded into a Mono-P HR 5/20 FPLC (Pharmacia) column pre-equilibrated with 25 mM bis-tris (pH 6.0) and 9% betaine at 23° C. After the baseline stabilized the column was eluted with 100 mL Polybuffer 74 (10 mL:90 mL $H_2O$, v:v) (pH 4.0) (Pharmacia), and 9% betaine at a flow rate of 1 mL/min. The collection tubes contained 100 μL 0.5 M tricine buffer (pH 7.0), and 50 mM DTT to give a final concentration in 1 mL of 50 mM tricine (pH 7.0), and 5 mM DTT in 1 min fractions. This in effect stabilized the final pH conditions for the proteins eluted under slightly acidic pH from the Mono-P column. The major activity for xanthosine-$N^7$-methyltransferase in collection tubes without tricine was found in fractions 15 and 16 of the gradient eluting from the column with a pH of 5.42 and 5.35 respectively. It was important not to freeze the protein samples at any stage of the purification, as this had a substantial negative effect on the activity state of xanthosine-$N^7$-methyltransferase.

B. Assay of Enzyme Activity

The 100 μL standard assay mixture contained 50 mM tricine (pH 7.0), 1200 μM xanthosine, 5 mM DTT, 7.5 μM S-adenosyl-L-[methyl-$^{14}$C]-methionine (SAM) (60 mCi/mmol; DuPont NEN), and 1 mM $Na_2EDTA$. The reaction mixture (50 μL without enzyme) was preincubated for 10 min at 25° C. and the reaction was initiated by the addition of 50 μL enzyme solution and allowed to proceed at 25° C. for 1 hour. At the end of the incubation period three 30 μL aliquots of the reaction were removed and terminated by adding to 8 μL of 0.6 M perchloric acid ($HClO_4$). The same was done for zero time controls in order to detect true enzymic activity. This mixture was centrifuged in a microcentrifuge for 5 min and 19 μL of the supernatant was mixed with 1.0 μL of 33 mM 7-methylxanthosine. These mixtures were spotted on Whatman No.1 chromatography paper and developed with n-butanol-acetic acid-$H_2O$ (n-BuOH-HOAc-$H_2O$) (4:1:1). The position of 7-methylxanthosine was determined by its blue fluorescence when exposed to short wavelength UV light. This region was cut out of the chromatograms and the radioactivity was determined by scintillation counting using 3 mL Scinti-verse scintillation fluid (Fisher Scientific). Counting efficiency was 74.7%. Background and non-specific radiation detected in the 7-methylxanthosine region of the zero time samples were subtracted.

C. Identification of the Reaction Product

The site of methylation on the xanthine ring was identified by hydrolysis of the sugar from the methylated xanthosine reaction product and separation in 4 different chromatography systems. The product from two 100 μL reactions done as described above and containing 6 μL of 33 mM 7-methylxanthosine as carrier, was applied as a band at the origin of a Whatman No.1 paper chromatogram. The chromatogram was developed in n-BuOH-HOAc-$H_2O$ (4:1:1). The region of the chromatogram corresponding to methylated xanthosine was detected as above, cut into small pieces, placed in a sterile tube, and incubated with 35 mL of deionized water at 37° C. with shaking overnight. The extract was filtered through 2 layers of miracloth followed by a 0.22μ filter and then lyophilized. The dried extract was resuspended in 1.0 mL of deionized water, placed in a glass digestion vial and lyophilized. The sample was resuspended in 400 μL of 1.0 M HCl and incubated for 1 hour at 100° C. The digest was lyophilized, resuspended in 400 μL of 3 mM 7-methylxanthine and again lyophilized. The digest was resuspended in 40 μL of deionized water, and 10 μl was chromatographed in each of four different systems. 1-Methylxanthine, 3-methylxanthine, 7-methylxanthine, 8-methylxanthine, 7-methylxanthosine, xanthine and xanthosine were included on each chromatogram for comparison. The following chromatography systems were used; Whatman No.1 paper developed in n-BuOH-HOAc-H$_2$O (4:1:1) and C8 thin layer plates (Whatman KC18F) developed in either isoamyl alcohol-H$_2$ O-acetonitrile (41:4:5), ethanol-H$_2$O (4:1) or tert-BuOH-HOAc-H$_2$O (4:1:1). After drying, the chromatograms were sprayed with En$^3$Hance (Dupont NEN), redried and exposed for 30 days to pre-flashed Fuji RX$_{GCU}$ X-ray film at −70° C.

D. Identification of Proteins by Gel Electrophoresis

Extracts obtained as above were used in single dimension (1D) SDS-PAGE minigels (main gel:12.5% acrylamide, 0.8% methylene bisacrylamide; stacking gel:7.5% acrylamide, 0.21% methylene bisacrylamide) by mixing with Laemmli sample buffer (Laemmli, U. K., *Nature* 227:680 (1970)), and in two-dimensional (2D) mini IEF/ SDS-PAGE by the modified method of O'Farrell et.al. (O'Farrell, P. Z., Goodman, H. M., O'Farrell P. H., *Cell* 12:1133 (1977)). Two-dimensional electrophoresis was made possible by precipitating proteins with 50 volumes of 100% ethanol for 1 hour and redissolving the proteins in isoelectric focusing (IEF) sample buffer containing 5% ampholines (1:1, v:v, pH 3–10:pH 5–7, LKB-Pharmacia). The ratio of the original protein extract to the IEF sample buffer was maintained at least 1:2 to ensure that any remaining buffer constituents from the chromatography steps did not interfere with IEF. Equal total protein samples (<20 μg) were applied to the basic end of prefocused tube gels (8.8% acrylamide, 1.6% methylene bisacrylamide) containing 5% ampholines as above. The gels were focused for 10,000 V-hours plus an additional 2 hours at 1,000 V. Blank focused gels were cut into 5 mm sections and incubated in 0.5 mL of 100 mM CaCl$_2$ for 24 hours, and the pH of the segments was determined. From this analysis, the pH gradient of the IEF gel was estimated to range from 4.4 to 6.0.

The tube gels were prepared for SDS-PAGE by a brief H$_2$O wash followed by three washes (10 min each) in hot Laemmli sample buffer. The tube gels were placed on the top of SDS-PAGE gels (main gel:12.5% acrylamide, 0.8% methylene bisacrylamide; stacking gel:7.5% acrylamide, 0.21% methylene bisacrylamide) and held in place with 3% agarose in Laemmli sample buffer. Proteins were visualized by silver-staining. In 1D gels the Mono-P fraction 16 which had the highest enzymic activity indicated only the presence of a doublet under silver staining (FIG. 2). The molecular weight of these proteins in kilo-Dalton's (kD) was approximately 37.6 and 36.1. In 2D gels each protein separated into two spots. The isoelectric point (IP) of the more acidic one had an average value over several gels of 5.2, and the more basic one of 5.3. Their molecular weight's however now averaged 43.5 kD, with the upper and lower peptides fusing into each other. Therefore, there is a distinct difference in kD between 1D and 2D gels. The similar migration of all these four peptides in Mono-P columns, 1D and 2D gels indicates that they are isozymes which may be post-translationally modified. Alternatively they may be products of a gene family which have slight differences in their structure from each other, resulting in the differing isozymes observed.

E. Protein Sequencing

Total protein estimation by the procedure of Lowry (Lowry, O. H., Rosebrough, N. J., Farr, A. L. and Randall, R. J., *J. Biol. Chem.* 193:265 (1951)) for fraction 16 of Mono-P indicated there was a total of 100 μg of protein in the 1 mL fraction. It is our experience that at these low concentrations of protein, Lowry values tend to be an over-estimation of the actual amount present. We decided to overcompensate for this by using a substantial part of this fraction for protein sequencing. A 900 μL portion of Mono-P fraction 16 representing 90 μg was placed in a sterile 1.5 mL microcentrifuge tube and 216 μL of 100% trichloro-acetic acid (TCA) was added to it. After mixing, the tube was allowed to incubate on ice overnight, and was then centrifuged at 14,000 rpm in a microcentrifuge for 30 min at 4° C. The supernatant was removed by aspiration, and the pellet washed twice with 1 mL of 75% ethanol, each washing being followed by a centrifugation step. The pellet was dried by placing the tube in a speedvac and spinning for 1 min under vacuum. The precipitate had 20 μL of 2×Laemmli sample buffer added to it. It was then boiled in a water bath for 5 min, and then microfuged for 1 min. When the tube temperature had cooled down to 23° C. the whole amount was loaded into a single lane of a 12.5% 1D gel. At the termination of electrophoresis proteins were visualized by staining with 0.1% Coomassie R-250 in aqueous 50% methanol and 10% acetic acid, (w:v:v), and then destained. The same doublet of 37.6 and 36.1 kD observed in silver stained gels was also visible in the Coomassie stained gels. The region of the gel comprising this doublet was cut out and used for protein sequencing by automated Edman degradation.

Protein sequencing was performed by the University of California, Davis, Protein Structure Laboratory standard protocol. The gel piece containing the doublet was washed 4 times with 15 mL of H$_2$O by shaking gently for 15 min to remove the acetic acid and SDS remaining from the previous steps. The gel piece was diced with a razor blade to 2 mm squares, and transferred to a 1.5 mL microcentrifuge tube. The gel pieces were dehydrated in a Speed-Vac for 2 hours until they did not adhere to the tube. Next 30 μL of gel rehydration buffer (0.1 M Tris-HCl, pH 9.0, 0.05% SDS) was added, and the pH verified at 8.0 by spotting 0.5 μL on pH paper. The digestion enzyme Lys-C (0.2 ug) from *Achromobacter lyticus* (Wako) was added, along with additional rehydration buffer to completely hydrate the gel pieces and leave a little extra buffer. The mixture was allowed to incubate overnight at 30° C. After the incubation period, the supernatant was removed to a fresh, sterile microcentrifuge tube and stored. Enough water was added to cover the gel pieces, and they were incubated for a further 2 hours at 30° C. The supernatant was removed and stored in the same microcentrifuge as before. This wash step was repeated once more, with the supernatants being combined with the previous two washes. The gel pieces were then covered with a solution comprising of 0.1% trifluoroacetic acid (TFA) in 80% acetonitrile, and incubated for 1 hour at 30° C. The supernatant was collected and added to the tube containing all the previous supernatants. The last wash was repeated once more, and the pooled supernatants were dried in a speed-vac.

The dried tryptic digestion products were dissolved in 25 µL of 6 M guanidine-HCl, 0.4 M tris (pH 8.2), and the pH verified by spotting 0.5 µL on pH paper. One µL of 450 mM DTT was added and the digest was incubated for 45 min at 50° C. After cooling to room temperature 2 µL of 500 mM iodoacetamide was added, and incubated for a further 15 min at 23° C. At the end of this incubation 72 µL of water was added to give a final concentration of 1.5 M guanidine, and 0.1 M tris. The sample was then centrifuged for 5 min at 14,000 rpm in a microcentrifuge and the supernatant was carefully removed to a new microcentrifuge tube. To the precipitated pellet 25 µL of 0.1% TFA vas added and vortexed. The tube was then re-centrifuged as before, and the supernatant added to that from the previous step.

The cleavage fragments from the tryptic digestion were resolved from each other by capillary high pressure liquid chromatography (HPLC) in a C18 1 mm×10 cm column, utilizing a linear gradient over 90 min of 5% solvent A (0.1% TFA) to 70% solvent B (0.075% acetonitrile) at a flow rate 100 µL per min. The UV detection was set at 210 nm with the scale ranging from 0 to 0.1 A. The recovery of individual peaks indicated the presence of several distinct peptides as shown in FIG. 3. As a control a portion of the original BDS-PAGE gel that did not contain protein was carried through the digestion process. The filled peaks shown in FIG. 3 were common between this control and the sample. The 3 peaks labelled A, B, and C were subjected to automated Edman degradation. Two of the peaks (A and B) yielded overlapping unique sequences representing the same protein fragment (FIG. 2, Fragments A and B). The third peak (C) yielded a different unique sequence (FIG. 2, Fragment C).

F. Synthesis of Oligonucleotide DNA Primers for Xanthosine-$N^7$-methyltransferase Chemical synthesis of 20 mer primers for the two amino acid sequences obtained by the digestion fragments of xanthosine-$N^7$-methyltransferase was done by The Midland Certified Reagent Company. Regions of the fragments selected had minimal nucleic acid degeneracy, and where possible amino acids that have extensive genetic code redundancy were avoided. Where this was not possible more than one primer was synthesized for the same fragment to include all of the possible alternative codon combinations. Furthermore, we also synthesized primers such that they were complementary to the coding strand of the DNA sequences which code for the amino acid sequence. Third position nucleotide degeneracies of three or more were overcome by using inosine at thse positions. Where the degeneracy of a nucleotide was two-fold, both nucleotides were included in primer synthesis (FIG. 3).

G. Extraction of RNA from B3 Stage Young Coffee Leaves

All items used during the extraction were sterile, RNase-free, and prepared by treating with 0.1% DEPC water. All centrifugation steps were carried out at 4° C. unless otherwise stated.

Young coffee leaves of the B3 stage were collected and stored as previously described. Total RNA was isolated from 100 g of this young leaf tissue by grinding under liquid nitrogen and immediately transferring into a prechilled domestic coffee grinder. The tissue was ground to powder together with a small piece of dry-ice. The tissue was then added to 200 mL of homogenization buffer made up of 100 mM tris-HCl (pH 9.0), 200 mM NaCl, 15 mM $Na_2EDTA$, 0.5% sarcosyl, and freshly added 100 mM β-mercaptoethanol. To this was added 200 mL buffer-equilibrated phenol, and 40 mL of a mixture of chloroform:isoamyl alcohol (24:1, v:v). The tissue was then homogenized in a glass beaker in an ice bath for 2 min at high speed in a Polytron homogenizer. Immediately after homogenization 14 mL 3 M sodium acetate (pH 4.0) was added and mixed by operating the homogenizer for an additional 1 min. The homogenate was then stored on ice for 15 min., and subsequently transferred into two 250 mL polypropylene centrifuge tubes. Centrifugation was performed in a GSA (DuPont Sorvall) rotor at 16,000×g for 10 min. The aqueous phase (top layer) was transferred to a new 250 mL polypropylene centrifuge tube and an equal volume of isopropanol was added to it.

This mixture was incubated overnight at −20° C. and then centrifuged at 10,000×g for 10 min to collect the precipitated RNA.

The RNA pellet was washed with 70% ethanol and re-centrifuged at 10,000×g for 5 min. The ethanol was decanted and the pellet dried under vacuum for 5 min. The pellet was then resuspended in 15 mL of DEPC-treated water. The RNA suspension was transferred into a sterile 40 mL screw-cap centrifuge tube and the insoluble material removed by centrifugation at 10,000×g for 5 min. The supernatant was transferred to a new 40 mL screw-cap centrifuge tube and 5 mL of 8 M LiCl was added to it to give a final concentration of 2 M LiCl. The tube was incubated overnight at 4° C. and the RNA was recovered by centrifugation at 14,000×g for 10 min. The RNA pellet was then washed with 70% ethanol, centrifuged at 10,000×g for 5 min, and briefly dried under vacuum. The pellet was resuspended in 5 mL DEPC-treated water and centrifuged at 10,000×g for 5 min to remove insoluble material. The supernatant was transferred into 4 sterile 1.5 mL microcentrifuge tubes and stored on ice. The quantitation of 10 µL of the total RNA solution in a Shimadzu UV 160U spectrophotometer in a 230 to 330 nm spectrum indicated that there was 42.8 mg of RNA. The tubes containing the RNA were stored at −70° C.

H. Purification of Poly ($A^+$) mRNA from Total RNA

The total RNA preparation was enriched for poly ($A^+$) RNA (mRNA) using the PolyATtract II mRNA isolation system kit (Promega Corporation). A 600 µL aliquot of the total RNA equalling 5.1 mg was added into a tube of the above mentioned kit and made to 2.43 mL final volume with RNase-free water. After heating at 65° C. for 10 min, 10 µl of 50 pmole/ml biotinylated oligo(dT) and 60 µl of 20×SSC (175.3 g/L NaCl, 88.2 g/L sodium citrate, pH 7.0) were added and the mixture was allowed to slowly cool to room temperature over a period of approximately 30 min. An aliquot of the streptavidin paramagnetic particles were washed 3 times in 0.5×SSC (1.5 µL per wash) and resuspended in 0.5 mL of 0.5×SSC. The RNA solution containing the biotinylated oligo(dT) was added to the washed streptavidin paramagnetic particles. After a 10 min incubation at room temperature, the paramagnetic particles along with the trapped mRNA were captured to the side of the tube using a magnet. The supernatant was removed and the particles were washed four times with 0.1×SSC (1.5 mL/wash). The mRNA was recovered by suspending the particles in 1.0 mL RNase-free water and removing the water while the particles were captured on the side of the tube. The water was placed, 500 µL at a time, into two 1.5 mL sterile microcentrifuge tubes. After the addition of ¹⁄₁₀th volume of 3 M sodium acetate (50 μL per tube), the mRNA was recovered by precipitation with an equal volume of isopropanol (550 μL per tube). The tubes were stored at −20° C. overnight and then centrifuged at 14,000 rpm for 30 min at 4° C. The pellet was washed with 500 μL of 75% ice-cold ethanol and re-centrifuged. The ethanol was decanted and the pellet dried briefly under vacuum. The mRNA was dissolved in 60 μL of DEPC-treated nuclease-free sterile water. Quantitation was performed on 15 μL of the dissolved mRNA as described for total RNA. Approximately 9.6 μg of mRNA was recovered from 5 mg of total RNA.

I. Construction of cDNA Library

First and second strand cDNA was synthesized using the ZAP-cDNA synthesis kit (Stratagene). Four μg of mRNA in 25 μL of water was incubated at 65° C. for 5 min. Three μL of 100 mM methyl mercury was added and incubated at room temperature for 10 min. Four μL of 700 mM β-mercaptoethanol was added and incubation was continued for an additional 5 min. To the denatured mRNA 5 μL of 10× first strand buffer, 5 μL of 100 mM DTT, 3 μL nucleotide mixture (10 mM each DATP, dGTP, TTP and 5-methyl-dCTP), 2 μL of 1.4 μg/mL linker-primer (5'GAGAGAGAGAGAGAGAGAGAACTAGTCTCGAG TTTTTTTTTTTTTTTTTT3'), 1 μL RNase block and 5 μL of water were added. The reaction was incubated at room temperature for 10 min to anneal the primer to the mRNA and 2.5 μL of 20 u/μL M-MuLV reverse transcriptase was added. Five μL of this reaction mixture was removed to a tube containing 0.5 μL of 800 Ci/mmole [a-$^{32}$P]dCTP (DuPont NEN). Both reactions were incubated at 37° C. for 1 hour. The radioactively labeled reaction was frozen at −20° C. for later gel analysis.

To the 45 μL main reaction 40 μL of second strand buffer, 15 μL of 100 mM DTT, 6 μL of nucleotide mixture (10 mM DATP, dGTP, TTP and 26 mM dCTP), 268.3 μL water and 2 μL of 800 Ci/mmol [α-$^{32}$P]dCTP was added. After mixing, 4.5 μL of 1 u/μL RNase H and 19.2 μL of 5.2 u/μl E. coli DNA polymerase I were added and the reaction was incubated at 16° C. for 2.5 hours. The reaction was extracted with 400 μL of phenol:chloroform (1:1) and the phases were separated by centrifugation. The aqueous phase was removed to a new tube and re-extracted with chloroform. The aqueous phase recovered as above. The double-stranded cDNA was recovered by precipitation overnight at −20° C. after the addition of 33.3 μL of 3M sodium acetate and 867 μL of 100% ethanol. The precipitate was recovered by centrifugation in a microcentrifuge at 4° C. for 60 min. The precipitate was washed with 1 μL of 80% ethanol and recovered by centrifugation at room temperature at full speed in a microcentrifuge. The supernatant was removed, the precipitate was dried under vacuum and dissolved in 45 μL of water. Three μL of the resuspended double-stranded cDNA was removed and frozen at −20° C. until analyzed by gel electrophoresis.

To the remaining 42 μL of the double-stranded cDNA 5 μL of 10×Klenow buffer (buffer #3), 2.5 μL of 2.5 mM nucleotides (dCTP, dGTP, dATP and TTP), and 0.5 μL of 5 u/μL Klenow fragment were added. After 30 min at 37° C., 50 μL of water were added and the reaction was extracted with an equal volume of phenol:chloroform (1:1) and then chloroform as described above. After the addition of 7 μL of 3M sodium acetate and 226 μL of 100% ethanol, the blunt-ended double-stranded DNA was recovered by precipitation by incubating on ice for 30 min and microcentrifuging at full speed at 4° C. for 60 min. The pellet was washed with 300 μL of 80% ethanol, centrifuged and dried as before. Seven μL of 0.4 μg/μL EcoRI linkers were added to the dried cDNA. The structure of the EcoRI linkers is:

5' AATTCGGCACGAG 3'
3' GCCGTGCTC 5'

After vortexing to resuspend the cDNA, 1 μL of 10× ligation buffer, 1 μL 10 mM ATP and 1 μL of 4 Weiss u/μL T4 DNA ligase was added and the reaction was incubated over night at 8° C. The ligase was inactivated by heating at 70° C. for 30 min. The 5' ends of the EcoRI linkers attached to the cDNA were phosphorylated using polynucleotide kinase. One μL of 10× buffer #3, 2 μL of 10 mM ATP, 6 ML of water and 1 ML of 10 u/ML T4 polynucleotide kinase were added to the ligation reaction. After 30 min at 37° C. the kinase reaction was heat inactivated at 70° C. for 30 min.

XhoI "sticky ends" were generated at the end of the cDNA corresponding to the 3' end of the mRNA by digestion of the XhoI site in the linker-primer (see above). Twenty-eight μL of XhoI buffer and 3 μL of 40 u/mL XhoI were added to the cDNA and the reaction was incubated at 37° C. for 1.5 hours. The cDNA with EcoRI sticky ends at the 5' end and XhoI sticky ends at the 3' end (relative to the original mRNA) were size fractionated by passage through a Sephacryl S-400 spin column as follows. Five μL of 10× STE (100 mM tris (pH 7.0), 5 mM EDTA and 100 mM NaCl) was added and the cDNA was applied to the top of a 1 μL syringe containing Sephacryl S-400. A 500 ml microcentrifuge tube was placed on the bottom of the syringe and the column was placed in a centrifuge tube and centrifuged at about 400×g for 2 min. Sixty μL of 10× STE was added to the top of the syringe, a new microcentrifuge tube was placed on the bottom and the column was again centrifuged as before. This process was repeated until six fractions had been collected.

About 10% of each fraction was electrophoresed on a 1% agarose gel to determine the size distribution of the cDNA in each fraction. The remainder of each fraction was extracted with an equal volume of phenol:chloroform and then chloroform as described above and then precipitated by the addition of 2 volumes of 100% ethanol. After incubation at −20° C. over night, the cDNA was recovered by centrifugation at 14,000 rpm at 4° C. for 60 min in a microcentrofuge. The cDNA was washed with 200 μL of 80% ethanol as described above and dried. The cDNA was dissolved in 5 μL of water and 0.5 μL was removed to determine the cDNA concentration by fluorography using the Hoefer TKO 100 DNA Fluorometer. The remaining 4.5 mL of fraction 1, containing the largest cDNA molecules, contained about 304 ng of cDNA.

One-hundred ng of cDNA from fraction 1 was ligated into 1 μg of Uni-Zap, a bacteriophage lambda ZAP vector that had been digested with EcoRI and XhoI (Stratagene). Fraction 1 cDNA (2.9 Ml) was added to 0.54 μL of 10×ligation buffer, 0.5 μL 10 mM ATP, 1 μL of 1 μg/μL Uni-Zap XR vector and 0.5 μL of 4 Weiss u/μL T4 DNA ligase. The reaction was incubated at 8° C. for about 44 hours. One μL aliquot of the ligation reaction was added to one aliquot of the 'Freeze-Thaw' extract from the Gigapack II Gold packaging kit (Stratagene). Fifteen μL of sonic extract was added and the contents were gently mixed. Packaging was carried out at room temperature. After 2 hours, 500 μL of SM buffer (0.01 M tris-HCL pH 7.5, 0.01 M MgCl$_2$ 0.1 mM Na$_2$EDTA) and 20 μL of chloroform was added to the packaging reaction, the debris was removed by a short centrifugation in a microcentrifuge and the packaged phages were stored at 4° C. until used.

J. Titering of Primary Library

One μL of the 500 μL primary library was mixed with 9 μL of SM buffer for a ⅒ dilution. One μL of this dilution was used to infect 200 μL of *E. coli* XL1-Blue MRF' cells grown to a density equal to an O.D.$_{600}$=0.5. The cells were incubated at 37° C. for 15 min with gentle shaking. The infected cells were then mixed with 2.5 mL of 48° C. top agar containing 15 μL of 0.5 M IPTG, and 50 μL of 250 mg/ml X-gal and plated on 100×15 mm NZY plates (5 g/L NaCl, 2 g/L MgSO$_4$.7H$_2$O, 5 g/L yeast extract, 10 g/L NZ amine [pH 7.5], and 15 g/L Difco agar). The plates were incubated overnight at 37° C. Background plaques were blue, while the recombinant plaques were white. The average of three such plates indicated that 1 μL of primary library produced 1,930 white recombinant plaques, and 65 blue plaques. The total 500 μL primary library was calculated to represent 965,000 recombinant plaques.

K. Amplification of Primary Library

Into 20 sterile tubes 300 μL of *E. coli* XL1-Blue MRF' cells grown to an O.D.$_{600}$=0.5 were added. To each tube 12.5 μL of primary library stock, and 90 μL of SM buffer were added and the tubes were incubated at 37° C. for 15 min. Two and one-half mL of 48° C. top agar was added to each tube and the cells were plated on 100×15 mm NZY plates. The plates were incubated overnight at 37° C. Five mL of SM buffer were added to each plate and the plates were incubated for a further 8 hours at 4° C. The SM buffer was collected with a sterile pipette and stored in a sterile 250 mL centrifuge tube. Each plate was washed with about 4 mL of fresh SM buffer which was added to the previously collected material. Chloroform, to a final volume of 5%, was added to the amplified library. The library was then incubated at room temperature for 15 min and then centrifuged at 2,000×g for 10 min to remove cell debris. The supernatant (114.5 mL) was recovered and then transferred to a sterile polypropylene bottle. Chloroform was added to a final volume of 0.3% and the amplified library was stored at 4° C.

L. Titration of Amplified Library

One μL of a $10^{-11}$ dilution of the amplified library in SM buffer contained 192 recombinant plaques when plated as described above. In order to obtain 50,000 recombinant plaques, 25 μL of a $10^{-7}$ dilution was used to infect 600 μL of *E. coli* XL1-Blue MRF' cells grown to an O.D.$_{600}$=0.5, which were then incubated at 37° C. for 15 min. To these cells 6.5 mL of 48° C. top agar was added and the library was plated on 150×15 mm NZY plates. Four such plates representing 200,000 recombinant plaques, were prepared and incubated at 37° C. overnight. The plates were then chilled for 4 hours at 4° C., and then used for DNA screening of the library.

M. Polymerase Chain Reaction (PCR) Amplification of Xanthosine-N$^7$-methy Transferase cDNA The synthesis of first strand cDNA was as described in the Stratagene protocol above. The two unique peptide sequences obtained by tryptic digestion allowed the synthesis of the degenerate primers depicted in FIG. 4. A polymerase chain reaction (PCR) (Saiki, R. K., Gelfand, D. H., Stoffel, S., Scharf, S. J., Higuchi, R., Horn, G. T., Mullis, K. B. and Erlich, H. A., *Science* 239:487 (1988)) between pairs of these primers (1–6, 2–6, 3–5 or 4–5) using 4 ng cDNA, 1 μL 20 μM primers, 0.5 μL of each 1 mM deoxyribonucleotide triphosphate, 1.5 mM MgCl$_2$, 0.3 μL Taq DNA polymerase [5,000 u/mL], 2.5 μL 10× PCR buffer [10 mM tris-HCl (pH 9.0), 0.1% triton X-100] and sterile H$_2$O to a final volume of 25 μL was carried out. PCR conditions were 94° C. for 4 min [1 cycle]; 94° C. for 1 min, 43° C. for 1 min, 72° C. for 1 min [35 cycles]; 72° C. for 5 min [1 cycle]). Reactions were done in 500 μL sterile microcentrifuge tubes using a Perkin Elmer DNA thermal cycler 480. Only the primer combination 1 and 6 resulted in a single product at an annealing temperature of 43° C. The product was measured by agarose gel electrophoresis using SeaPlaque agarose (FMC) to be approximately 750 base pairs. A commercially available 100 bp ladder was used as a size marker (Promega Corporation).

M. Cloning of Coffee-specific Xanthosine-N$^7$-methyltransferase PCR Gene Product The 750 bp fragment obtained using primers 1 and 6 (FIG. 4) in a 50 μL PCR reaction had 50 μL of chloroform, and 100 μL of sterile water added to it. The mixture was vortexed and then centrifuged in a microcentrifuge at 14,000 rpm for 2 min. The top aqueous layer containing the DNA was removed and placed in a sterile tube. Ethidium-bromide plate quantitation indicated the presence of about 5 ng of about PCR amplfied DNA/μL. The PCR product was then ligated into a TA Cloning Kit pCR II vector (Invitrogen Corporation) in a 10 μL ligation reaction containing 1 μL 10×ligation buffer, 2 μL pCR II vector (25 ng/μL), 3 μL fresh PCR product (5 ng/μL), 1 μL T4 DNA Ligase, and 3 μL of sterile water. The ligation reaction was incubated at a 14° C. overnight. The ligation reactions were centrifuged at 14,000 rpm for 2 min and placed on ice. To a freshly thawed vial of *E. coli* XL1-Blue competent cells 2 μL of 0.5 M β-mercaptoethanol was added and mixed gently with the pipette tip. Two μL of the ligation reaction was pipetted into the cells and they were stirred gently with the pipette tip to mix. The vial was then incubated on ice for 30 minutes and heat shocked for exactly 30 seconds in a 42° C. heat-block. The vial was placed on ice. After 2 min 450 μL of sterile SOC medium (20 g/L tryptone, 5 g/L yeast extract, 0.5 g/L NaCl, 10 mL/L 250 mM KCl, 10 mL/L MgCl$_2$, 20 mL/L 1 M glucose, [pH 7.0]) was added to it. The vial was subsequently shaken at 225 rpm in a rotary shaker for 1 hour and then the placed on ice.

The transformed cells were plated by pipetting 50 μL and/or 200 μL from the cell suspension onto one of two LB plates (10 g/L tryptone, 5 g/L yeast extract, 10 g/L NaCl, 15 g/L Difco agar, pH 7.5) containing 50 μg/mL ampicillin and 40 μg/mL X-Gal. The plates were incubated at 37° C. for 20 hours and then moved to 4° C. for 3 hours to allow color development. Six white transformant colonies were analyzed for the presence and orientation of the PCR fragment.

N. Boiling Plasmid Mini-prep

Each of the transformant colonies was grown in 5 mL sterile terrific broth (12 g/L tryptone, 24 g/L yeast extract, 4 mL/L glycerol, 100 mL/L 10× TB phosphate [0.17 M KH$_2$PO$_4$, 0.72 M K$_2$HPO$_4$]) supplemented with 50 μg/mL ampicillin. The tubes were incubated overnight in a rotary shaker at 37° C. Three mL of each colony was transferred to a 1.5 mL microcentrifuge tube, 1 mL at a time, and the cells concentrated by centrifugation at 14,000 rpm for 2 min. The supernatant was discarded each time and the cell pellet left as dry as possible. The cells were washed one time with 1 mL of sterile H$_2$O and centrifuged as before. The supernatant was discarded and the cell pellet resuspended in 320 μL STET buffer (8% sucrose, 0.5% triton X-100, 50 mM EDTA, 10 mM tris-HCl, pH 8.0). To these cells, 32 μL of 10 mg/mL lysozyme in TE buffer (10 mL/L 1 M tris-HCl pH 8.0, 2 mL/L 0.5 M EDTA pH 8.0) was added and mixed by inverting the tubes several times. The tubes were placed in a boiling water bath for 5 min, and then placed immediately on ice. Once cooled they were centrifuged for 30 min at 14,000 rpm at 4° C. The pellet was removed from each tube with a sterile toothpick. The supernatant had 170 µL of 7.5 M NH₄OAc and 550 µL of ice-cold isopropanol added to it, and the DNA was precipatated overnight at −20° C. The tubes were centrifuged at 14,000 rpm at 4° C. for 30 min, and the pellet washed with 75% ethanol and dried for 1 min in a speed-vac. The DNA was resuspended in 50 µL of sterile H₂O containing 1 µL of 5 mg/mL RNase A.

O. Restriction Digestion to Remove Insert from pCR II Plasmid

A reaction mixture of 25 µL was prepared by adding 15 µL of plasmid mini-prep DNA as obtained above, 2.5 µL of buffer H (90 mM tris-HCl [pH 7.5], 10 mM MgCl₂, 50 mM NaCl), 1 µL of EcoRI (8–12 u/µL), and 6.5 µL of sterile H₂O. The mixture was incubated in a shaking water bath at 37° C. for 1 hour, and then boiled in a water bath for 1 min. The tubes were centrifuged at 14,000 rpm for 15 seconds and then allowed to cool down to room temperature. To 10 µL of each mixture 2 µL of loading dye was added, and the digestion products were analyzed by 1.5% agarose gel electrophoresis using ultra-pure agarose (GibcoBRL) and a 100 bp ladder as a size marker (Promega Corporation).

Only one of the six reactions indicated the presence of a digested insert of ~750 bp. The original bacterial colony corresponding to the plasmid with the 750 bp xanthosine-$N^7$-methyl transferase PCR product was inoculated into a 250 mL Erlenmayer flask containing 50 mL of sterile LB media (10 g/L tryptone, 5 g/L yeast extract, 10 g/L NaCl, pH 7.5) supplemented with 50 µg/mL ampicillin. The flask was incubated in a rotary shaker at 30° C. overnight. In a 1.5 mL microcentrifuge tube 18 mL of the resulting cell media was concentrated by centrifugation as above.

Plasmid DNA was purified using the QIAGEN plasmid mini kit procedure (Qiagen Inc.). The washed bacterial pellet was resuspended in 0.3 mL of buffer P1 which contains the supplied RNase. To this 0.3 mL of alkaline lysis buffer P2 was added, mixed gently by flicking the tube and incubated for no longer than 5 min at room temperature. Next 0.3 mL of chilled buffer P3 was added and mixed by inverting the tube 6 times. After 10 minsutes on ice the extract was centrifuged 14,000 rpm for 15 min in a microcentrifuge. The supernatant was removed and applied to a QIAGEN-tip 20 that was previously equilibrated by the application of 1 mL QBT buffer by gravity flow. The applied cell extract supernatant was also allowed to enter the resin of the column by gravity flow. Once the flow through the column had stopped, the QIAGEN-tip 20 was washed 4 times with one mL buffer QC. The DNA was eluted by washing the QIAGEN-tip 20 with 0.8 mL buffer QF and precipitated by the addition of 0.7 volumes (560 µL) of room temperature isopropanol. The tube was immediately centrifuged at 14,000 rpm for 30 min and the supernatant carefully removed. The precipitated DNA was washed with 1 mL of ice-cold 70% ethanol, centrifuged as above, and air dried for 5 min. The DNA was resuspended in 100 µL of sterile H₂O. UV spectrophotometry, as described above, on 1 µL of the DNA resuspension indicated that there was 55 µg of purified recombinant pCRII plasmid DNA per 100 µL.

Automated DNA sequencing of the insert in the pCRII plasmid from its 5' end was accomplished using the M13 reverse primer which binds to a reference in pCRII just adjacent to the site where the PCR product was inserted.

Sequencing was done at the University of Hawaii Biotechnology service facility. The sequencing reaction contained 1 µg of plasmid template and 3.2 pmol M13 primer. The sequence obtained indicated that the PCR product coded for the DNA sequence of the first 6 amino acids of peptide fragments A and B (FIG. 4) from whose sequence the degenerate DNA primers 1 and 2 (FIG. 4) were made. In addition, the sequence also coded for the following 7 amino acids of the peptide fragment, the DNA sequence of which was not used in primer construction. So in effect the DNA sequence for the correct protein was cloned.

P. Making of a Random Primed Probe for cDNA Screening Using the PCR Product

Two 25 µL restriction digestions with EcoR1 were carried out on two 17.5 µL aliquots of the purified pCRII plasmid as described above. The products were separated on a 1% agarose gel as before, and the 750 bp insert was excised aseptically from two lanes of the gel. The gel pieces having a mass of 0.65 g were transferred into a sterile 40 mL polypropylene tube and subjected to Geneclean II kit purification (BIO 101, Inc). Four and one-half volumes of NaI (2.93 mL) stock solution was added to the gel slices. One-half the volume of the gel TBE modifier (325 µL) was added and the tube incubated at 45° C. for 5 min. To this 15 µL of glassmilk suspension was added and incubated for a further 5 min. The glassmilk/DNA complex was pelleted by centrifugation for 10 sec at 1,000 rpm and the supernatant was removed. The glassmilk pellet was washed 3 times with 1 mL New Wash solution and the DNA was eluted with 50 µL of sterile H₂O. Ethidium bromide plates indicated that the DNA concentration was 10 ng/µL.

A random primed probe was systhesized from 30 ng (3 µl) of the purified DNA. Three µl of the DNA was added to 27 µL of sterile water and the DNA was denatured by heating in a boiling water bath. To this the Promega Corporations Prime-a-Gene kit constituents (10 µL 5× labeling buffer, 2 µL of unlabeled dNTP's [20 µM each dCTP, dGTP, TTP], 2 µL 1 mg/mL acetylated BSA, 1 µL 5u/µL Klenow enzyme) and 5 µL of [α-$^{32}$P]DATP (50 µCi, 3,000 Ci/mmole; DuPont NEN) were added to a final volume of 50 µL, and allowed to incubate at room temperature for 1 hour. The reaction was terminated by the addition of 2 µL 0.5 M Na₂EDTA (20 mM final concentration) and heated for 2 min in a boiling water bath.

Q. Screening of Amplified Library with Random Primed Probe

The four 150×15 mm NZY plates that had approximately 50,000 recombinant clones per plate were chilled to 4° C. (see above for plating and growth conditions), and the recombinant plaques lifted by first presoaking 132 mm Magna nylon transfer membranes (MSI Corporation) on chromatography paper saturated with 5× SSC buffer for 10 sec. The membranes were placed onto the plates containing the recombinant plaques for 5 min, and then lifted and placed, phage containing side up, for 2 min on chromatography paper saturated with 0.5 M NaOH and 1.5 M NaCl. The membranes were neutralized by transferring onto chromatography paper saturated with 0.5 M tris-HCl (pH 8.0) and 1.5 M NaCl for 5 min. They were then placed for 20 sec on chromatography paper saturated with 2× SCC buffer, 0.2 M tris-HCL (pH 7.5) and then blotted dry. After 1 hour of air drying, the DNA was cross-linked to the membranes by exposure to 12,000 µJoules of UV using a UV Stratalinker 1800 (stratagene Corporation). The four membranes were prehybridized at 65° C. for 2 hours in 100 mL 6× SSPE (52.2 g/L NaCl, 8.3 g/L $NaH_2PO_4 \cdot H_2O$, 2.2 g/L $Na_2$EDTA, [pH 7.4]), 5× Denhardt's solution (1 g/L Ficoll, 1 g/L polyvinylpyrrolidone, 1 g/L BSA [pentax fraction V]), 0.5% SDS and 100 μg/mL denatured herring sperm DNA in a Hybrid Mark II hybridization oven.

Hybridization was carried out at 65° C. for 12 hours in 10 mL of 6× SSPE, 0.5% SDS, 100 μg/mL powdered/denatured herring sperm DNA, and 52 μL 15×10⁶ dpms/ml of the random primed probe described above. At the end of the hybridization period the probe was removed and the membranes briefly washed for 30 sec with 100 mL of 65° C. 2× SSC containing 0.5% SDS. The membranes were then washed for an additional 30 min with the same amount and concentration of fresh buffer. The membranes were subjected to two more 100 mL washes for 30 min with 65° C. 0.2× SSC, 0.5% SDS, and then rapped in a cellophane envelope and exposed to pre-flashed Fuji $RX_{GCU}$ X-ray film at −70° C. for 24 hours. Fifteen positive clones were observed. These plaques were picked and placed in 1 mL SM buffer containing 20 μL chloroform (phage stock). Of these, 11 were processed to secondary or tertiary screening until single individual plaques were obtained.

R. Characterization of Xanthosine-$N^7$-methyltransferase cDNA Clones

The sizes of the putative xanthosine-$N^7$-methyltransferase cDNA clones were determined by polymerase chain reaction using primers homologous to the T3 and T7 promoters that are present in the cloning vector and that flank the cDNA insertion site. Conditions for polymerase chain reaction were as described above except that the cycle was 35 cycles of 95° C. for 1 minute, 50° C. for 1 minute and 72° C. for 2 minutes. Analysis was by agarose gel electrophoresis as before. The three largest clones obtained were subjected to in vivo excision by mixing in a sterile tube 200 μL of single plaque phage stock with 200 μL of fresh XL1-Blue MRF' cells grown to an O.D.$_{600}$=1.0. To this mixture 1 μL of ExAssist (Stratagene Corporation) helper phage (>1×10⁶ pfu/μL) was added and the tubes were incubated at 37° C. for 15 min. Three mL of sterile LB broth was added and incubation was continued for 3 hours at 37° C. with shaking. The cultures were heated in a 70° C. water bath for 20 min, and then the tubes centrifuged at 1,000×g for 15 min. One mL of the supernatant containing the excised pBluesript phagemid packaged as a filamentous phage particle was transferred to a sterile 1.5 mL microcentrifuge tube and stored at 4° C. as the stock solution. Twenty-five μL of the stock solution was added to 200 μL of *E. coli* Solar cells grown to an O.D.$_{600}$=1 in a microcentrifuge tube. After incubation at 37° C. for 15 min, the 200 μL cells were plated on 100×15 mm NZY agar plates containing 50 μg/mL ampicillin. The plates were incubated overnight at 37° C. until colonies appeared. A single colony was inaculated into 10 mL of sterile LB broth containing 50 μg/mL ampicillin and grown overnight at 37° C. with shaking. The 10 mL of cell culture was concentrated in a 1.5 mL sterile microcentrifuge tube and the pelleted cells subjected to QIAGEN plasmid purification as described previously. The purified plasmid DNA was resuspended in 50 μL of sterile $H_2O$. DNA automated sequencing reactions were performed by mixing 8 μL of this DNA sample (0.8 μg) with 4 μL of either T3 or T7 sequencing primers (0.8 pmol/μL). The remainder of the process was as previously described. Each sequencing reaction gave aproximately 350 bases of sequence. The sequence is shown in FIG. 5. Thre amino acid sequence of xanthosine-$N^7$ -methyl transferase as predicted from the base sequence of the cDNA is shown in FIG. 6.

The foregoing examples are for illustrative purposes only, and should not be viewed as limiting the scope of applicants' invention, which is set forth in the claims appended hereto.

```
                        SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
           (A) LENGTH: 15 amino acid residues
           (B) TYPE: amino acid
           (C) STRANDEDNESS: Not Relevant
           (D) TOPOLOGY: linear (ii) MOLECULE TYPE:
           (A) DESCRIPTION: peptide (v) FRAGMENT TYPE: Internal fragment (ix) FEATURE:
           (A) NAME/KEY: Fragment A
           (D) OTHER INFORMATION:  Xaa means undetermined (xi) SEQUENCE DESCRIPTION: SEQ ID NO:1:

Ile Asn Tyr Ala Ser Gly Ala Ser Gly Ile Leu Asp Gln Xaa Gly
        1               5                  10                  15

(2) INFORMATION FOR SEQ ID NO:2:
```

```
    (i) SEQUENCE CHARACTERISTICS:
        (A) LENGTH: 14 amino acid residues
        (B) TYPE: amino acid
        (D) TOPOLOGY: linear (ii) MOLECULE TYPE:
        (A) DESCRIPTION: peptide (xi) SEQUENCE DESCRIPTION: SEQ ID NO:2:

Ile Asn Tyr Ala Ser Gly Ala Ser Gly Ile Leu Asp Gln Thr
    1               5                   10

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: primer (v) FRAGMENT TYPE: Internal fragment (ix) FEATURE:
        (D) OTHER INFORMATION:  N is inosine (xi) SEQUENCE DESCRIPTION:  SEQ ID NO:3:

ATNAAYTAYG CNAGYGGNGC                                                    20

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nuclear acid
        (A) DESCRIPTION:  primer (v) FRAGMENT TYPE: Internal fragment (ix) FEATURE:
        (D) OTHER INFORMATION:  N is inosine (xi) SEQUENCE DESCRIPTION: SEQ ID NO:4:

ATNAAYTAYG CNAGYGGNGC                                                    20

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: primer (v) FRAGMENT TYPE: internal (ix) FEATURE:
        (D) OTHER INFORMATION:  N is inosine (xi) SEQUENCE DESCRIPTION: SEQ ID NO:5:

CGNCCAGNCG NYTAYTTNAT                                                    20

(2) INFORMATION FOR SEQ ID NO:6:
```

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION:  primer (v) FRAGMENT TYPE: Internal fragment (ix) FEATURE:
            (D) OTHER INFORMATION:  N is inosine (xi) SEQUENCE DESCRIPTION: SEQ ID NO:6:

CGNCCYCTYG CYTAYTTNAT                                                          20

(2) INFORMATION FOR SEQ ID NO:7:

(i) SEQUENCE CHARACTERISTICS:
            (A) LENGTH: 14 amino acid residues
            (B) TYPE: amino acid
            (C) STRANDEDNESS: single
            (D) TOPOLOGY: linear (ii) MOLECULE TYPE:
            (A) DESCRIPTION: peptide (v) FRAGMENT TYPE: Internal fragment (ix) FEATURE:
            (D) OTHER INFORMATION: Xaa is either Thr or
                Asp (xi) SEQUENCE DESCRIPTION: SEQ ID NO:7:

Gln Tyr Val Pro Cys Tyr Phe Xaa Phe Ile Asp Asp Gln Asp
     1               5                  10

(2) INFORMATION FOR SEQ ID NO: 8:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION:  primer (v) FRAGMENT TYPE: Internal fragment (ix) FEATURE:
            (D) OTHER INFORMATION:  N is inosine (xi) SEQUENCE DESCRIPTION: SEQ ID NO:8:

CAWTATGTNC CNTGTTATTT                                                          20

(2) INFORMATION FOR SEQ ID NO: 9:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION:   primer (v) FRAGMENT TYPE: Internal fragment (ix) FEATURE:
            (D) OTHER INFORMATION:  N is inosine (xi) SEQUENCE DESCRIPTION: SEQ ID NO:9:

AAWTAWCAHG GNACWTATTG                                                                            20

(2) INFORMATION FOR SEQ ID NO:10:

(i) SEQUENCE CHARACTERISTICS:
        (A) LENGTH: 371 amino acid residues
        (B) TYPE: amino acid
        (C) STRANDEDNESS: single
        (D) TOPOLOGY: linear (ii) MOLECULE TYPE:
        (A) DESCRIPTION: protein (xi) SEQUENCE DESCRIPTION: SEQ ID NO:10:

```
Met Ala Phe Val Ala Arg Gln Trp Phe Leu Leu Ser Ile Ile Asn
 1               5                  10                  15

Val Val Val Val Cys Phe Leu Lys Pro Phe Ala Leu Gly Glu Gln
                20                  25                  30

Gln Val Pro Cys Tyr Phe Ile Phe Gly Asp Ser Gln Asp Asp Asn
                35                  40                  45

Gly Asn Asn Asn His Leu Asn Thr Thr Ala Arg Ala Asn Tyr Pro
                50                  55                  60

Pro Tyr Gly Ile Asp Phe Pro Glu Gly Pro Thr Gly Arg Phe Thr
                65                  70                  75

Asn Gly Arg Asn His Ala Asp Phe Ile Gly Glu Leu Leu Gly Phe
                80                  85                  90

Asp Ser Tyr Ile Pro Pro Phe Ala Asn Thr Lys Gly Arg Asp Ile
                95                 100                 105

Thr Lys Gly Ile Asn Tyr Ala Ser Gly Ala Ser Gly Ile Leu Asp
               110                 115                 120

Gln Thr Gly Arg His Leu Gly Asp Leu Phe Ser Phe Asn Glu Gln
               125                 130                 135

Leu His Asn His Glu Arg Ala Ile Ser Arg Ile Val Arg Leu Ile
               140                 145                 150

Gly Asn Arg Ser Ala Thr Lys Glu Tyr Leu Ala Lys Cys Leu Tyr
               155                 160                 165

Thr Val Ala Leu Gly Asn Asn Asp Tyr Ile Asn Asn Tyr Leu Leu
               170                 175                 180

Pro Glu Tyr Tyr Pro Thr Ser His Leu Tyr Thr Pro Arg Glu Phe
               185                 190                 195

Ala Ser Leu Leu Ile Arg His Tyr Ser Gln Gln Leu Arg Thr Leu
               200                 205                 210

Tyr Arg Leu Gly Ala Arg Lys Ile Ala Val Phe Gly Leu Gly Trp
               215                 220                 225

Leu Gly Cys Ile Pro Ala Glu Leu Ser Thr Asp Gly Asn Cys Val
               230                 235                 240

Asp Ser Ile Asn Glu Glu Val Leu Leu Phe Asn Asp Lys Leu Lys
               245                 250                 255

Pro Leu Val Asp Glu Leu Asn Thr Glu Leu Ser Gly Ala Gln Phe
               260                 265                 270

Leu Tyr Val Asp Val Ile Ala Ile Asn Leu Asn Asn Leu Ser Thr
               275                 280                 285

Pro Ala Glu Ile Thr Ile Gly Asn Ala Pro Cys Cys Asn Val Ser
               290                 295                 300

Ala Ala Val Ala Gly Gly Gln Cys Ile Pro Gly Gln Ile Pro Cys
```

```
                    305                 310                 315
        Ser Asn Arg Asn Gln Tyr Tyr Phe Trp Asp Asp Phe His Pro Ser
                    320                 325                 330

Glu Val Val Asn Glu Ala Tyr Ser Arg Leu Ala Tyr Ser Ala Leu
                    335                 340                 345

Ser Ser Leu Leu Asp Ala Asp Pro Leu Ala Ile Gly Gly Leu Thr
                    350                 355                 360

Gly Lys Asn Cys His Asp Lys Val Lys Ile Gln
                    365                 370

(2) INFORMATION FOR SEQ ID NO:11:

(i) SEQUENCE CHARACTERISTICS:
        (A) LENGTH: 1347 base pairs
        (B) TYPE: nucleic acid
        (C) STRANDEDNESS: single
        (D) TOPOLOGY: linear (ii) MOLECULE TYPE: cDNA to mRNA (ix) FEATURE:
        (A) NAME/KEY:CDS
        (B) LOCATION:53..1168

(xi) SEQUENCE DESCRIPTION: SEQ ID NO:11:

CCTCTGACTT GCTAAACCTA CCATTACCTT TTTCTTCTTG TCATCTGCAT TC              52

ATG GCT TTT GTA GCC AGG CAA TGG TTT CTC CTA TCC ATC ATT               94
Met Ala Phe Val Ala Arg Gln Trp Phe Leu Leu Ser Ile Ile
  1               5                  10

AAT GTA GTG GTT GTC TGT TTC TTG AAA CCA TTT GCC CTA GGC               136
Asn Val Val Val Val Cys Phe Leu Lys Pro Phe Ala Leu Gly
 15                  20                  25

GAA CAA CAG GTC CCT TGC TAC TTC ATT TTT GGA GAC TCA CAA               178
Glu Gln Gln Val Pro Cys Tyr Phe Ile Phe Gly Asp Ser Gln
         30                  35                  40

GAT GAC AAT GGC AAC AAT AAT CAC CTG AAC ACC ACT GCC AGG               220
Asp Asp Asn Gly Asn Asn Asn His Leu Asn Thr Thr Ala Arg
             45                  50                  55

GCA AAT TAT CCA CCT TAC GGC ATT GAT TTC CCA GAA GGT CCA               262
Ala Asn Tyr Pro Pro Tyr Gly Ile Asp Phe Pro Glu Gly Pro
                 60                  65                  70

ACT GGT CGC TTC ACC AAT GGT CGA AAT CAT GCA GAC TTC ATT               304
Thr Gly Arg Phe Thr Asn Gly Arg Asn His Ala Asp Phe Ile
                     75                  80

GGT GAG CTC CTT GGA TTT GAC AGC TAC ATA CCT CCA TTT GCA               346
Gly Glu Leu Leu Gly Phe Asp Ser Tyr Ile Pro Pro Phe Ala
 85                  90                  95

AAT ACA AAA GGC CGG GAT ATC ACT AAA GGC ATT AAT TAT GCT               388
Asn Thr Lys Gly Arg Asp Ile Thr Lys Gly Ile Asn Tyr Ala
100                 105                 110

TCG GGA GCA TCT GGA ATT CTT GAT CAG ACC GGT CGT CAC CTG               430
Ser Gly Ala Ser Gly Ile Leu Asp Gln Thr Gly Arg His Leu
         115                 120                 125

GGC GAT CTC TTC AGC TTC AAC GAA CAA TTG CAC AAT CAC GAG               472
Gly Asp Leu Phe Ser Phe Asn Glu Gln Leu His Asn His Glu
             130                 135                 140

AGA GCA ATT TCG CGC ATC GTG CGG TTG ATT GGA AAC AGA TCT               514
Arg Ala Ile Ser Arg Ile Val Arg Leu Ile Gly Asn Arg Ser
                 145                 150

GCA ACA AAA GAA TAT CTA GCC AAA TGT CTG TAC ACT GTT GCA               556
Ala Thr Lys Glu Tyr Leu Ala Lys Cys Leu Tyr Thr Val Ala
```

-continued

```
155                 160                 165
TTG GGG AAT AAT GAT TAC ATC AAC AAC TAC TTG TTG CCA GAA        598
Leu Gly Asn Asn Asp Tyr Ile Asn Asn Tyr Leu Leu Pro Glu
        170                 175                 180

TAT TAT CCT ACC AGC CAC CTA TAT ACT CCA AGA GAA TTT GCC        640
Tyr Tyr Pro Thr Ser His Leu Tyr Thr Pro Arg Glu Phe Ala
            185                 190                 195

AGC TTG TTA ATT AGG CAT TAT TCT CAG CAA CTA CGG ACT TTG        682
Ser Leu Leu Ile Arg His Tyr Ser Gln Gln Leu Arg Thr Leu
                200                 205                 210

TAC AGA TTG GGG GCA AGA AAA ATA GCC GTT TTT GGG CTT GGT        724
Tyr Arg Leu Gly Ala Arg Lys Ile Ala Val Phe Gly Leu Gly
                    215                 220

TGG CTT GGC TGC ATA CCT GCT GAG TTA TCT ACA GAT GGT AAC        766
Trp Leu Gly Cys Ile Pro Ala Glu Leu Ser Thr Asp Gly Asn
225                 230                 235

TGT GTG GAT TCT ATT AAC GAG GAA GTT CTG TTA TTC AAT GAC        808
Cys Val Asp Ser Ile Asn Glu Glu Val Leu Leu Phe Asn Asp
        240                 245                 250

AAG CTC AAG CCA CTG GTT GAT GAA CTG AAT ACC GAG TTA AGC        850
Lys Leu Lys Pro Leu Val Asp Glu Leu Asn Thr Glu Leu Ser
            255                 260                 265

GGT GCA CAA TTT CTT TAT GTA GAT GTG ATA GCA ATC AAT TTG        892
Gly Ala Gln Phe Leu Tyr Val Asp Val Ile Ala Ile Asn Leu
                270                 275                 280

AAC AAT TTA TCC ACC CCT GCA GAA ATT ACA ATT GGC AAT GCA        934
Asn Asn Leu Ser Thr Pro Ala Glu Ile Thr Ile Gly Asn Ala
                    285                 290

CCA TGC TGC AAC GTG TCT GCA GCA GTT GCT GGT GGA CAG TGT        976
Pro Cys Cys Asn Val Ser Ala Ala Val Ala Gly Gly Gln Cys
295                 300                 305

ATT CCT GGG CAA ATT CCC TGC AGC AAC AGG AAC CAA TAT TAT        1018
Ile Pro Gly Gln Ile Pro Cys Ser Asn Arg Asn Gln Tyr Tyr
        310                 315                 320

TTT TGG GAT GAT TTC CAT CCC AGT GAA GTA GTC AAT GAA GCA        1060
Phe Trp Asp Asp Phe His Pro Ser Glu Val Val Asn Glu Ala
            325                 330                 335

TAT TCA AGA TTA GCA TAT TCT GCG TTA TCC TCA TTA CTT GAT        1102
Tyr Ser Arg Leu Ala Tyr Ser Ala Leu Ser Ser Leu Leu Asp
                340                 345                 350

GCT GAT CCT CTT GCC ATT GGC GGC CTA ACA GGC AAA AAC TGT        1144
Ala Asp Pro Leu Ala Ile Gly Gly Leu Thr Gly Lys Asn Cys
                    355                 360

CAT GAT AAA GTG AAG ATA CAA TAGACTGTAT CTATGTGTCC              1185
His Asp Lys Val Lys Ile Gln
365                 370

CATGATATTT CTATATTCCA AGTTTCCGAC AAGTCAAACT CAATGTAATA         1235

AAACTTGAGA GTCCGAATGT GCTAGTGTGA TGTTATCTCC TCAATGGAAA         1285

CAATATGTTA TCATTAATCT CAGACTATTT ATAATTACTA TTAAAAAAAA         1335

AAAAAAAAAA AA                                                  1347
```

What is claimed is:

1. A substantially pure nucleic acid sequence that codes on expression for a coffee plant xanthosine-$N^7$-methyltransferase.

2. The nucleic acid sequence of claim 1, that comprises (i) the nucleotide sequence: (SEQ ID NO:11), or (ii) a nucleic acid sequence that is an allelic variant of the nucleic acid sequence: (SEQ ID NO:11).

3. A transforming vector comprising a transcription promoter operably linked to:

(a) the nucleic acid sequence: (SEQ ID NO:11); or (b) a nucleic acid sequence that codes on expression for the amino acid sequence: (SEQ ID NO:10); or (c) a nucleic acid sequence that is an allelic variant of the nucleic acid sequence: (SEQ ID NO:11).

4. The transforming vector of claim 3, wherein the nucleic acid sequence is operably linked to the transcription promoter in an antisense orientation.

5. The transforming vector of claim 3, wherein the promoter is a cauliflower mosaic virus 35S promoter.

6. The transforming vector of claim 3, wherein the vector is a modified plasmid pBI-121.

7. A coffee plant cell transformed with a nucleic acid sequence that codes on transcription for an RNA that is antisense to the mRNA that codes on expression for a xanthosine-$N^7$-methyltransferase having the amino acid sequence: (SEQ ID NO:10), wherein the RNA has a length sufficient to interfere with the expression of xanthosine-$N^7$-methyltransferase.

8. The transformed coffee plant cell of claim 7, wherein the cell exhibits reduced caffeine production compared to a coffee plant cell that is not transformed with the nucleic acid sequence.

9. The transformed coffee plant cell of claim 8, wherein the coffee plant cell is *Coffea arabica*.

10. A method for inhibiting production of caffeine by a coffee plant cell, comprising the steps of:
   providing a transforming vector comprising a nucleic acid sequence that codes on transcription for an RNA that has a length sufficient to interfere with the expression of a coffee plant xanthosine-$N^7$-methyltransferase, wherein the nucleic acid sequence is operably linked to a transcription promoter in an antisense orientation; and
   inserting the transforming vector into a coffee plant cell, wherein the nucleic acid sequence thereafter becomes inserted into the genome of the coffee plant cell to form a transformed cell, and wherein the transformed cell exhibits a reduced caffeine production compared to a coffee plant cell that has not been transformed with the nucleic acid sequence.

11. The nucleic acid sequence of claim 1, wherein the coffee plant is *Coffea arabica*.

12. The nucleic acid sequence of claim 1, wherein the xanthosine-$N^7$-methyltransferase comprises the amino acid sequence: (SEQ ID NO:10).

13. A coffee plant transformed with a nucleic acid sequence that codes on transcription for an RNA that is antisense to the mRNA that codes on expression for a coffee plant xanthosine-$N^7$-methyltransferase, wherein the RNA has a length sufficient to interfere with the expression of the xanthosine-$N^7$-methyltransferase.

14. The coffee plant of claim 13, wherein the nucleic acid sequence comprises (SEQ ID NO:11).

15. A coffee bean from the coffee plant of claim 13.

16. A coffee plant transformed with an isolated nucleic acid sequence that codes on expression for the amino acid sequence: (SEQ ID NO:10).

17. The coffee plant of claim 16, wherein the nucleic acid sequence is linked to a transcription promoter in an antisense orientation.

18. A transformed coffee plant produced by the process of inserting into the plant genome a nucleic acid sequence that codes on transcription for an RNA that is antisense to the mRNA that codes on expression for a xanthosine-$N^7$-methyltransferase having the amino acid sequence: (SEQ ID NO:10).

19. A coffee bean from the coffee plant of claim 18.

20. A coffee plant cell transformed with a nucleic acid sequence that codes on transcription for an RNA that is antisense to the mRNA that codes on expression for xanthosine-$N^7$-methyltransferase, wherein the RNA has a length sufficient to interfere with the expression of a coffee plant xanthosine-$N^7$-methyltransferase.

21. The coffee plant cell of claim 20, wherein the xanthosine-$N^7$-methyltransferase comprises the amino acid sequence: (SEQ ID NO:10).

22. A coffee plant regenerated from the coffee plant cell of claim 20.

23. A coffee bean from the coffee plant of claim 22.

24. A transformed coffee plant cell produced by the process of providing a transformation vector comprising a nucleic acid sequence that codes on transcription for an RNA that has a length sufficient to interfere with the expression of xanthosine-$N^7$-methyltransferase wherein the nucleic acid sequence is operably linked to a transcription promoter, and inserting the transforming vector into a coffee plant cell, wherein the nucleic acid sequence thereafter becomes inserted into the genome of the coffee plant cell to produce a transformed coffee plant cell.

25. The transformed coffee plant cell of claim 24, wherein the nucleic acid sequence is linked to the transcription promoter in an antisense orientation.

26. The transformed coffee plant cell of claim 24, wherein the transformed cell exhibits reduced caffeine production compared to a coffee plant cell that is not transformed with the nucleic acid sequence.

27. The transformed coffee plant cell of claim 24, wherein the coffee plant cell is *Coffea arabica*.

28. A coffee plant regenerated from the transformed coffee plant cell of claim 24.

29. A coffee bean from the coffee plant of claim 28.

30. A coffee plant cell transformed with an isolated nucleic acid sequence that codes on expression for the amino acid sequence: (SEQ ID NO:10).

31. The transformed coffee plant cell of claim 30, wherein the nucleic acid sequence is operably linked to a transcription promoter in an antisense orientation.

32. The transformed coffee plant cell of claim 30, wherein the transformed cell exhibits reduced caffeine production compared to a coffee plant cell that is not transformed with the nucleic acid sequence.

33. The transformed coffee plant cell of claim 30, wherein the coffee plant cell is *Coffea arabica*.

34. A coffee plant regenerated from the transformed coffee plant cell of claim 30.

35. A coffee bean from the coffee plant of claim 34.

36. A coffee bean from the coffee plant of claim 16.

37. A coffee plant regenerated from the transformed coffee plant cell of claim 7.

38. A coffee bean from the coffee plant of claim 37.

39. The transformed coffee plant cell of claim 20, wherein the cell exhibits reduced caffeine production compared to a coffee plant cell that is not transformed with the nucleic acid sequence.

40. A coffee plant transformed with a nucleic acid sequence that codes on transcription for an RNA that is antisense to the mRNA that codes on expression for xanthosine-$N^7$-methyltransferase, wherein the RNA has a length sufficient to interfere with the expression of a coffee plant xanthosine-$N^7$-methyltransferase.

41. The transformed coffee plant of claim 40, wherein the cell exhibits reduced caffeine production compared to a coffee plant cell that is not transformed with the nucleic acid sequence.

42. A coffee bean from the coffee plant of claim 40.

* * * * *

UNITED STATES PATENT AND TRADEMARK OFFICE
CERTIFICATE OF CORRECTION

PATENT NO. : 6,075,184
DATED : June 13, 2000
INVENTOR(S) : John I. Stiles, Istefo Moisyadi and Kabi Raj Neupane It is certified that error appears in the above-identified patent and that said Letters Patent is hereby corrected as shown below:

Column 19,
1. Please delete "(xi) SEQUENCE DESCRIPTION: SEQ ID NO : 3 :
    ATNAAYTAYG CNAGYGGNGC    20"
   and insert --
        (xi)    SEQUENCE DESCRIPTION: SEQ ID NO : 3 :
            ATNAAYTAYG CNTCNGGNGC    20 --.

2.  Please delete "(xi) SEQUENCE DESCRIPTION: SEQ ID NO : 5 :
        CGNCCAGNCG NYTAYTTNAT    20"
    and insert --
        (xi)    SEQUENCE DESCRIPTION:    SEQ ID NO : 5 :
            CGNCCNGANG CRTARTTNAT    20" --.

Columns 19, 20 and 21,
3.  Please delete "(xi) SEQUENCE DESCRIPTION: SEQ ID NO : 6 :
        CGNCCYCTYG CYTAYTTNAT    20"
    and insert --
    (xi)    SEQUENCE DESCRIPTION: SEQ ID NO : 6 :
        CGNCCRCTNG CRTARTTNAT    20 --.

4.  Please delete "(xi) SEQUENCE DESCRIPTION: SEQ ID NO : 8 :
        CAWTATGTNC CNTGTTATTT    20"
    and insert --
        (xi)   SEQUENCE DESCRIPTION: SEQ ID NO : 8 :
            CARTATGTNC CNTGTTATTT    20 --.

UNITED STATES PATENT AND TRADEMARK OFFICE
CERTIFICATE OF CORRECTION

PATENT NO.   : 6,075,184
DATED        : June 13, 2000
INVENTOR(S)  : John I. Stiles, Istefo Moisyadi and Kabi Raj Neupane It is certified that error appears in the above-identified patent and that said Letters Patent is hereby corrected as shown below:

5. Please delete "(xi) SEQUENCE DESCRIPTION: SEQ ID NO : 9 :
   AAWTAWCAHG GNACWTATTG    20"
   and insert --
   (xi)   SEQUENCE DESCRIPTION: SEQ ID NO : 9 :
   AARTARCANG GNACRTATTG    20 --.

Signed and Sealed this

Ninth Day of July, 2002

Attest:

JAMES E. ROGAN
Attesting Officer      Director of the United States Patent and Trademark Office